(12) United States Patent
Itou

(10) Patent No.: US 9,329,139 B2
(45) Date of Patent: May 3, 2016

(54) COMPLEX INSPECTION DEVICE FOR PRINTED-SUBSTRATE

(71) Applicant: YAMAHA HATSUDOKI KABUSHIKI KAISHA, Shizuoka-ken (JP)

(72) Inventor: Yasumichi Itou, Shizuoka (JP)

(73) Assignee: Yamaha Hatsudoki Kabushiki Kaisha, Shizuoka-ken (JP)

(*) Notice: Subject to any disclaimer, the term of this patent is extended or adjusted under 35 U.S.C. 154(b) by 149 days.

(21) Appl. No.: 14/370,054

(22) PCT Filed: Dec. 25, 2012

(86) PCT No.: PCT/JP2012/008278
§ 371 (c)(1),
(2) Date: Jun. 30, 2014

(87) PCT Pub. No.: WO2013/105194
PCT Pub. Date: Jul. 18, 2013

(65) Prior Publication Data
US 2015/0204801 A1    Jul. 23, 2015

(30) Foreign Application Priority Data

Jan. 12, 2012    (JP) .................... 2012-004381

(51) Int. Cl.
*G01N 23/04*    (2006.01)
*H05K 13/08*    (2006.01)
(Continued)

(52) U.S. Cl.
CPC ............ *G01N 23/04* (2013.01); *G01B 11/0608* (2013.01); *G01N 21/8806* (2013.01);
(Continued)

(58) Field of Classification Search
CPC ............ G01B 11/0608; G01B 21/956; G01B 21/8806; G01B 23/04; G01B 23/043; G01B 2021/95638; G01B 2201/12; G01B 2201/06113; G01B 2223/6113; G01B 15/025; G01B 15/02; G01B 15/00; H05K 3/00; H05K 13/08; A61B 6/032; G01N 23/04; G01N 23/06
See application file for complete search history.

(56) References Cited

U.S. PATENT DOCUMENTS 5,541,856 A * 7/1996 Hammermeister .... G01N 23/16
324/501
5,836,504 A * 11/1998 Koike .................... B23K 31/12
228/103

(Continued)

FOREIGN PATENT DOCUMENTS

CN    101706458 A    5/2010
JP    02-052246 A    2/1990
(Continued)

OTHER PUBLICATIONS

International Search Report; PCT/JP2012/008278; Mar. 26, 2013.
(Continued)

*Primary Examiner* — Hoon Song
(74) *Attorney, Agent, or Firm* — Studebaker & Brackett PC

(57) ABSTRACT

A complex inspection device provided with an optical image pickup unit, an X-ray camera, and an X-ray irradiation unit is provided. An arrival path is defined as a route of an X-ray that arrives at the X-ray camera from the X-ray irradiation unit. The arrival path is shortened for a close-up in a close-up position. In a non-close-up position, the arrival path is longer than that in the close-up position. When the X-ray irradiation unit and/or the X-ray camera needs to move toward the close-up position, the optical pickup unit is moved out in advance so that the X-ray irradiation unit and the X-ray camera relatively move toward the close-up position.

8 Claims, 16 Drawing Sheets

(51) Int. Cl.
  *G01B 11/06*  (2006.01)
  *G01N 21/88*  (2006.01)
  *G01N 21/956* (2006.01)
  *H05K 3/00*   (2006.01)
(52) U.S. Cl.
  CPC ............ *G01N21/956* (2013.01); *G01N 23/043* (2013.01); *H05K 13/08* (2013.01); *G01N 2021/95638* (2013.01); *G01N 2201/06113* (2013.01); *G01N 2201/12* (2013.01); *G01N 2223/6113* (2013.01); *H05K 3/00* (2013.01)

(56) References Cited

U.S. PATENT DOCUMENTS

| 6,314,201 | B1 | 11/2001 | Roder | |
|---|---|---|---|---|
| 2011/0255660 | A1* | 10/2011 | Masuda | G01N 23/04 378/22 |
| 2012/0321033 | A1* | 12/2012 | Stearns | G01N 21/763 378/4 |

FOREIGN PATENT DOCUMENTS

| JP | 11-295242 | A | 10/1999 |
|---|---|---|---|
| JP | 2002-350731 | A | 12/2002 |
| JP | 2004-340631 | A | 12/2004 |
| JP | 2010-085251 | A | 4/2010 |
| WO | 2009-078415 | A1 | 6/2009 |

OTHER PUBLICATIONS

The extended European search report issued by the European Patent Office on Feb. 24, 2016, which corresponds to European Patent Application No. 12864934.0-1905 and is related to U.S. Appl. No. 14/370,054.

* cited by examiner

FIG.14

| OPERATION | | INWARD CONVEYANCE AND RECEPTION OPERATION | CLAMP SUBSTRATE | MOVE TO IMAGING AREA | WITHDRAWAL OPERATION | MOVE TO CLOSE-UP POSITION | TRANSMISSIVE INSPECTION (CLOSE-UP) | CHANGE θ AND MOVE TO OBLIQUE IMAGING POSITION | TRANSMISSIVE INSPECTION (OBLIQUE) | MOVE SUBSTRATE TABLE | EXTERNAL INSPECTION | MOVE TO OUTWARD CONVEYANCE POSITION | RELEASE CLAMP ON SUBSTRATE | OUTWARD CONVEYANCE OPERATION |
|---|---|---|---|---|---|---|---|---|---|---|---|---|---|---|
| STEP | | S1 | S2 | S3 | S501 | S502 | S503 | S505 | S506 | S508 | S510 | S8 | S9 | S10 |
| TABLE DRIVE MECHANISM 100 | X AXIS MOTOR 114b | | | | | | | | | | | | | |
| | Y AXIS MOTOR 141b | | | | | | | | | | | | | |
| CONVEYOR UNIT 70 | CLAMP UNIT 75 | | | | | | | | | | | | | |
| X-RAY CAMERA UNIT 40 | X AXIS MOTOR 44a | | | | | | | | | | | | | |
| | Y AXIS MOTOR 48a | | | | | | | | | | | | | |
| | X-RAY CAMERA 50 | | | | | | | | | | | | | |
| X-RAY IRRADIATION APPARATUS 160 | Z AXIS MOTOR 155b | | | | | | | | | | | | | |
| | R AXIS MOTOR 170 | | | | | | | | | | | | | |
| OPTICAL IMAGING APPARATUS 300 | X AXIS MOTOR 185b | | | | | | | | | | | | | |
| | CCD CAMERA 301 | | | | | | | | | | | | | |

NON-CLOSE-UP
POSITION

CLOSE-UP
POSITION

COMPLEX INSPECTION DEVICE FOR PRINTED-SUBSTRATE

CROSS REFERENCE TO RELATED APPLICATIONS

This applications claims benefit of priority to Japanese Patent Application No. 2012-004381 filed on Jan. 12, 2012, and to International Patent Application PCT/JP2012/008278 filed on Dec. 25, 2012, the entire content of each of which is incorporated herein by reference.

TECHNICAL FIELD

The present disclosure relates to a complex inspection device for a printed substrate.

BACKGROUND

For inspecting a printed substrate on which a plurality of electronic components is mounted, a complex inspection device is known. As disclosed in Japanese Patent Application Publication No. H2-52246 and Japanese Patent Application Publication No. 2004-340631, the device is configured to achieve both transmissive inspection using X rays and external inspection using visible light.

The complex inspection device is provided with an X-ray imaging apparatus for transmissive inspection and an optical imaging apparatus for external inspection.

Regarding the X-ray imaging apparatus, Japanese Patent Application Publication No. H2-52246, for example, discloses an X-ray source and an X-ray image sensor of which the relative opposition interval with respect to the X-ray source is adjustable. Regarding the optical imaging apparatus, Japanese Patent Application Publication No. H2-52246 also discloses a mirror which is integrally movable with the X-ray imaging apparatus, and a vidicon tube which is fixed to the X-ray imaging apparatus and captures images of an inspection object portion via a mirror.

Regarding another X-ray imaging apparatus, Japanese Patent Application Publication No. 2004-340631 discloses an X-ray source (X-ray irradiation unit) and an X-ray imaging unit (CCD camera) which oppose each other via an electronic component which is an inspection object. Regarding the optical imaging apparatus, Japanese Patent Application Publication No. 2004-340631 also discloses a mirror being arranged coaxially between the electronic component and the X-ray irradiation unit, and an imaging apparatus which captures images by receiving light, which is reflected by the mirror, from an electronic component. The X-ray irradiation unit of Japanese Patent Application Publication No. 2004-340631 is disposed fixedly. An object substrate or an inspection object on which electronic components are mounted is configured to be movable in a perpendicular plane with respect to the direction of X-ray radiation from the X-ray irradiation unit.

According to the devices in the aforementioned prior art, it is possible to dispose the mirror on the path of the X-rays traveling through the inspection object portion, and to carry out simultaneously transmissive inspection by X-rays and external inspection by an optical camera, so that there is an advantage of improving inspection efficiency.

SUMMARY

However, in recent printed substrates, electronic components are integrated into a very compact size at high density, so that the locations to be inspected are getting dramatically smaller. As a result, even if either arrangement in the prior art is used, a close-up X-ray image taken at the magnification demanded in recent years has been unavailable for all of the inspection items.

Initially, regarding the arrangement of Japanese Patent Application Publication No. H2-52246, it is possible to change magnification as such, because the image sensor capturing X-ray images is configured to change the relative opposition interval between the image sensor and the X-ray source. However, in the arrangement of Japanese Patent Application Publication No. H2-52246, since the mirror is configured to move integrally with the image sensor immediately below it, the interposition of the mirror between the image sensor and the electronic component as an inspection object would tightly increase restriction of close-up image capturing, so that it could be difficult to obtain the required enlargement magnification.

Meanwhile, in the arrangement according to Japanese Patent Application Publication No. 2004-340631, the X-ray irradiation unit forming the X-ray source and the CCD camera forming the X-ray imaging unit are fixedly arranged, and the arrangement is merely configured such that the object substrate or an inspection object on which electronic components are mounted is to be movable in a perpendicular plane with respect to the direction of X-ray radiation from the X-ray irradiation unit. Therefore, it is inherently impossible to change the magnification of the X-ray image. Furthermore, in the arrangement according to Japanese Patent Application Publication No. 2004-340631, the mirror is likewisely interposed between the X-ray irradiation unit and the CCD camera to carry out coaxial imaging. As a result, even if the arrangement were incorporated with such an arrangement as disclosed in Japanese Patent Application Publication No. H2-52246, close-up images having a large magnification would have been unobtainable due to the interruption of the mirror.

The present disclosure has been devised in view of the problems described above, an object thereof being to provide a complex inspection device for a printed substrate whereby a close-up X-ray image captured at a prescribed enlarging magnification is available.

In order to resolve the problems described above, the present disclosure is a complex inspection device for a printed substrate, including: a substrate table configured to place a printed substrate on which a plurality of electronic components is mounted; an optical imaging apparatus configured to capture an optical image of an inspection object portion of the printed substrate placed on the substrate table; an X-ray irradiation unit configured to irradiate X-rays onto the inspection object portion; an X-ray camera configured to capture an X-ray image of the inspection object portion from X-rays traveling through the printed substrate; magnification changing means for changing a magnification of the X-ray image by relatively displacing the X-ray irradiation unit and the X-ray camera within a range between a close-up position where an arrival path of X-rays arriving at the X-ray camera from the X-ray irradiation unit has a first distance for close-up imaging, and a non-close-up position where the arrival path has a distance longer than the first distance; drive means for moving the optical imaging apparatus between an imaging position where the optical imaging apparatus faces the inspection object portion at a space between the X-ray irradiation unit and the X-ray camera, and a withdrawn position to which the optical imaging apparatus is moved out from the imaging position so that the X-ray irradiation unit and the X-ray camera are enabled to relatively move toward the close-up position; and imaging position control means for controlling the drive means such that, where at least one of the X-ray irradiation unit and the X-ray camera is required to move, the optical imaging apparatus is moved out in advance to the withdrawn position. In this mode, where the optical imaging apparatus is in the imaging position during inspection of a printed substrate on which a plurality of electronic components is mounted, it is possible, similarly to the prior art technology, to achieve external inspection based on images of visible light captured by the optical imaging apparatus, and transmissive inspection based on X-ray images captured by the X-ray camera, in parallel fashion, on the same printed substrate. Moreover, in the present mode, since the magnification of the X-ray images can be switched by the magnification changing means, then it is possible to respond to various imaging requirements which have been demanded in recent years. In addition, the optical imaging apparatus according to the present embodiment is configured to be movable between an imaging position and a withdrawn position for moving out from the imaging position, by drive means. If it is necessary to move the X-ray irradiation unit and the X-ray camera to the close-up position, then the drive means is controlled such that the optical imaging apparatus is moved out to the withdrawn position by the imaging position control means, and therefore it is possible to lower the X-ray irradiation unit close to the printed substrate and thus move same to the close-up position, without being obstructed by the optical imaging apparatus. Consequently, it is possible to obtain close-up X-ray images of even higher magnification which have been required in recent years.

A further mode of the present disclosure comprises: an optical imaging apparatus disposed above a printed substrate on which a plurality of electronic components are mounted, the optical imaging apparatus including an optical system having a light receiving unit permitting transmission of X-rays, the optical imaging apparatus being configured to capture an optical image of an inspection object portion obtained from the optical system; an X-ray irradiation unit configured to irradiate X-rays onto the inspection object portion from above; an X-ray camera configured to capture an X-ray image of the inspection object portion by receiving X-rays, traveling through the printed substrate, below the printed substrate; a lifting apparatus configured to adjust a height of the X-ray irradiation unit with respect to the printed substrate, within a range between a non-close-up position defined as a position above the optical imaging apparatus and a close-up position set below the optical system of the optical imaging apparatus; drive means for moving the optical imaging apparatus between an imaging position where the optical imaging apparatus is placed at a position at which the light receiving unit enables transmitting X-rays from the X-ray camera, the position being defined within a region from the X-ray irradiation unit located at the non-close-up position to the X-ray camera, and a withdrawn position where the optical imaging apparatus is moved outside the region; and imaging position control means for controlling the drive means such that the optical imaging apparatus is moved out in advance to the withdrawn position, in a case where the X-ray irradiation unit is driven to move between the close-up position and the non-close-up position by the lifting apparatus, wherein the X-ray camera is configured to capture X-ray images of the inspection object portion on the printed substrate which is disposed inside the region, in both cases where the X-ray irradiation unit is in the non-close-up position and where the X-ray irradiation unit is in the close-up position, and wherein the optical imaging apparatus is configured to capture optical images of the inspection object portion in the imaging position in a case where the X-ray irradiation unit is in the non-close-up position. According to this mode, both the capture of X-ray transmissive images and the capture of images by the optical imaging apparatus can be carried out simultaneously in parallel fashion, if the X-ray irradiation unit is located in the non-close-up position, while the printed substrate is held at a uniform position. Where the X-ray irradiation unit is in the close-up position, the X-ray irradiation unit does not collide with the optical imaging apparatus because the optical imaging apparatus enables moving out to a withdrawn position outside the region. Furthermore, where the X-ray irradiation unit captures X-ray transmissive images located at the close-up position, images of the same inspection object portion will be captured. Therefore, high accurate inspection can be performed on the basis of images of three types, namely, a non-close-up X-ray image, a close-up X-ray image and an optical image, captured at the inspection object portion.

As described above, according to the present disclosure, a marked beneficial effect is obtained in that when carrying out external inspection using visible light by an optical imaging apparatus and X-ray transmissive inspection by an X-ray imaging apparatus, with the same apparatus, it is possible to obtain a close-up X-ray image at a desired large magnification.

Further characteristics, objects, arrangements and actions and effects of the present disclosure can readily be understood from the following detailed description which should be read in conjunction with the accompanying drawings.

BRIEF DESCRIPTION OF THE DRAWINGS

FIG. 14 is a timing chart showing an operational sequence of FIG. 12 and FIG. 13.

DETAILED DESCRIPTION

Below, a preferred mode of implementing the present disclosure is described in detail with reference to the accompanying drawings. In the description given below, the respective parts relative to a complex inspection device 10 according to an embodiment of the present disclosure are described on the basis of an orthogonal coordinates system, in which an X axis is defined to coincide with a conveyance direction of a printed substrate W or an inspection object, a Y axis is defined as a horizontal direction perpendicular to the X axis, and a Z axis is defined as a vertical (up/down) direction. A large number of electronic components are mounted on the printed substrate W, and the conducting portions of the components are soldered. The complex inspection device 10 of the present embodiment is a device configured to inspect the suitability or unsuitability of the printed substrate W of which soldered portions are subjected as a main inspection object part.

Figure 1:
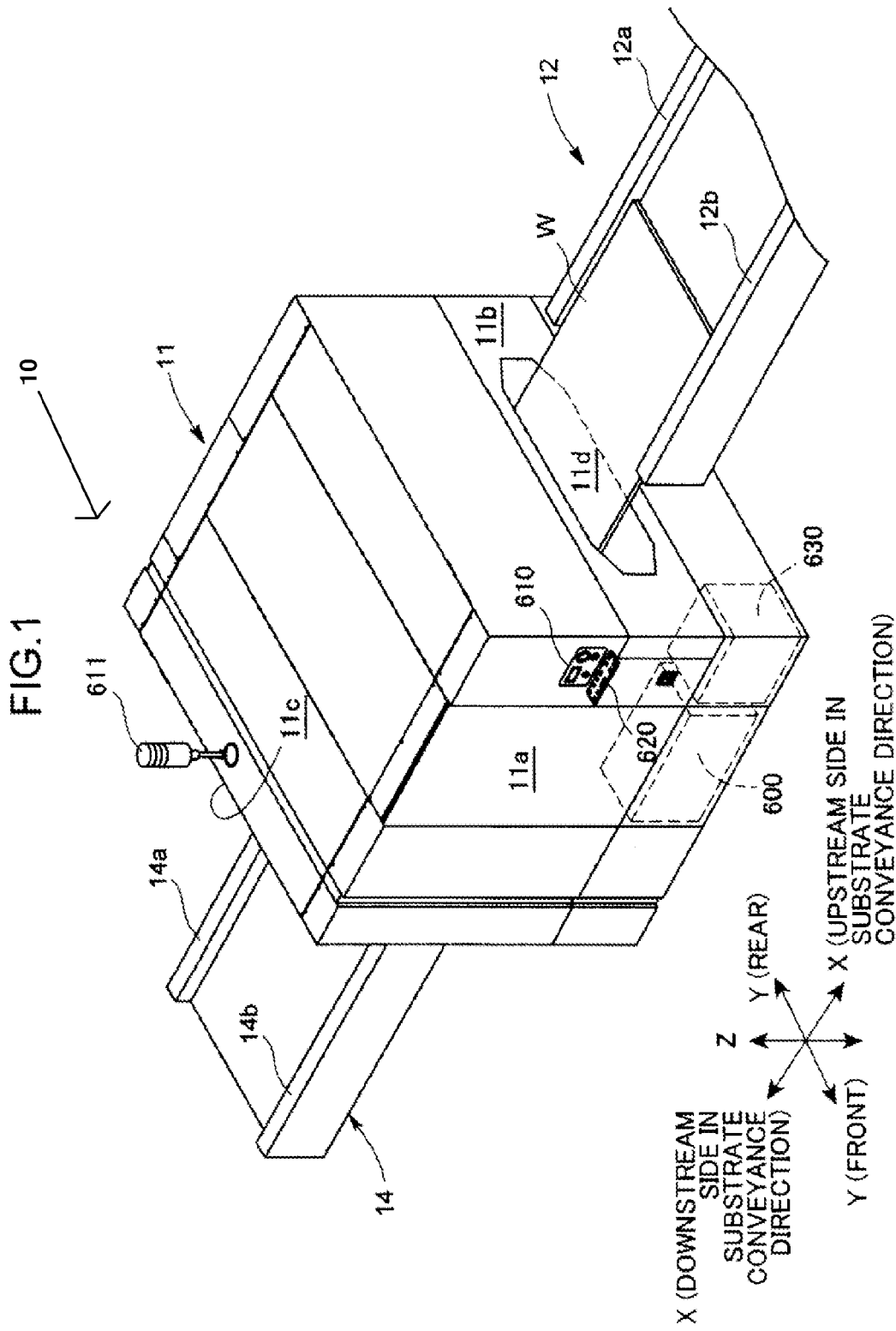
FIG. 1 is a perspective view showing an external appearance of a complex inspection device relating to one embodiment of the present disclosure.

Referring to FIG. 1, the complex inspection device 10 is provided with a housing 11 which is shielded with lead, or the like. The housing 11 is substantially cuboid in shape and a front surface 11a thereof faces towards one end of the Y axis direction. A pair of substrate conveyance conveyors 12, 14 for carry-in and carry-out of the substrate W is provided at either side of the housing 11. Each of the pair of substrate conveyance conveyors 12, 14 is configured by a pair of belt conveyors 12a, 12b and a pair of belt conveyors 14a, 14b. One of the substrate conveyance conveyors 12, 14 may be used as a substrate carry-in conveyor and the other thereof may be used as a substrate carry-out conveyor, in accordance with the specification of the equipment where the device is installed. In the example shown in the drawings, the substrate conveyance conveyor 12 on the right-hand side in FIG. 1 is a carry-in side, and the substrate conveyance conveyor 14 on the left-hand side is a carry-out side. In the equipment where the complex inspection device 10 is installed, a printed substrate W which has been carried-in from the substrate carry-in conveyor is introduced inside the housing 11. After the inspection, the printed substrate W is carried-out from the complex inspection device 10 by the substrate carry-out conveyor. Walls 11b and 11c at which the housing 11 opposes the printed circuit conveyance conveyors 12, 14 are respectively provided with a shutter mechanism such that a printed substrate W is carried-in and carried-out via substrate carry-in and carry-out ports 11d, 11e (see FIG. 2) which are opened and closed by these shutter mechanisms.

Figure 2:
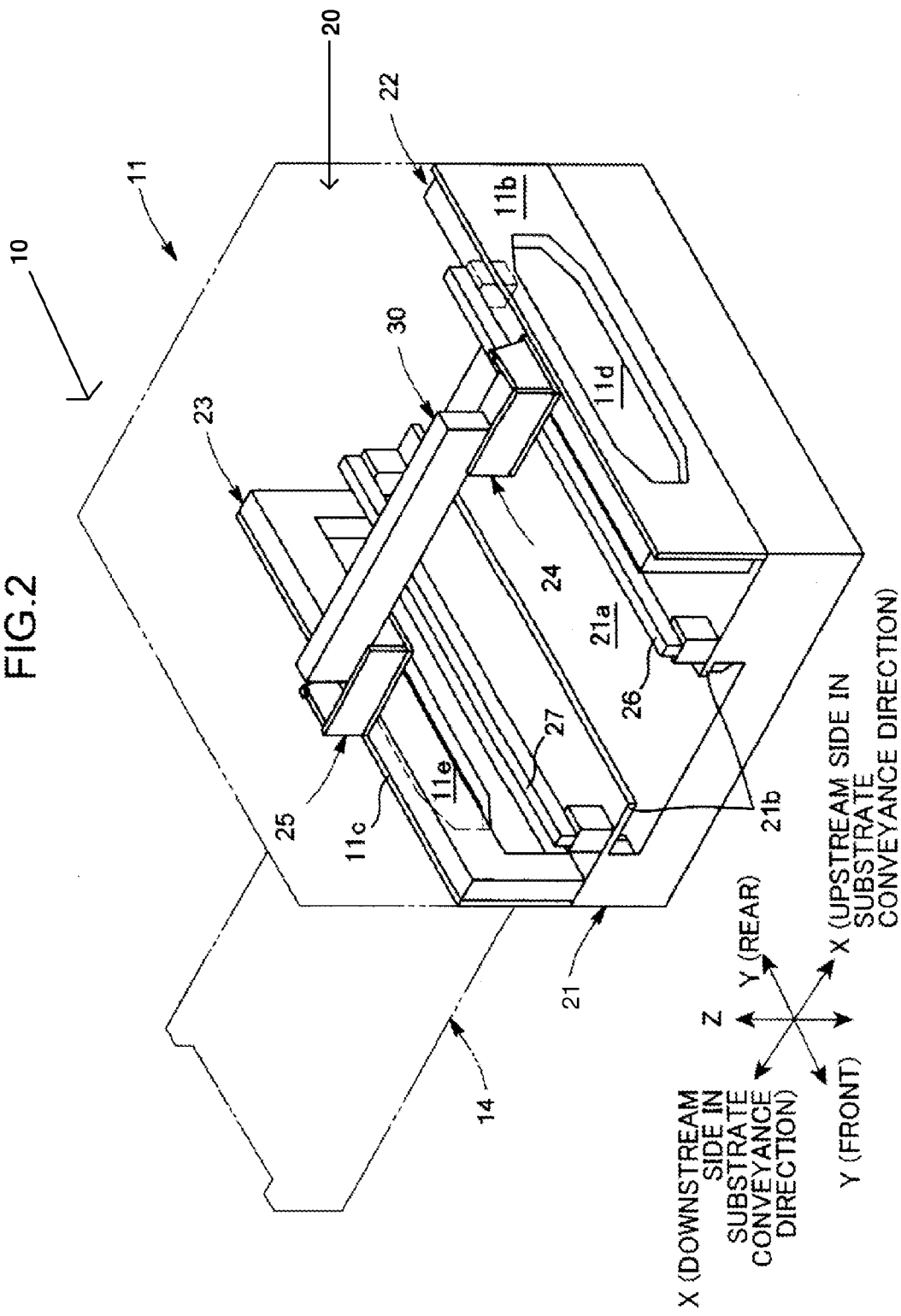
FIG. 2 is a perspective diagram showing a structure of the complex inspection device in FIG. 1.

Referring to FIG. 2, a structure 20 is installed inside the housing 11 for supporting the apparatuses provided in the complex inspection device 10. The structure 20 is provided with a base platform 21 which forms a bottom portion of the housing 11, a pair of gate sections 22, 23 standing on a top of the base platform 21 and respectively reinforcing inner wall portions at one end side and the other end side in the X axis direction, a pair of frame sections 24, 25 fixed to the center of an upper portion of each gate section 22, 23, and a beam 30 which spans between the two frame sections 24, 25. The respective parts of the structure 20 are each formed by combining various steel materials and/or plate metal members.

A bottom section 21a is formed on the base platform 21 such that the center with respect to the X axis is formed into a square shape extending in the Y axis direction. An X-ray camera unit 40, which is described hereinafter, is installed inside the bottom section 21a (see FIG. 3). Shelf sections 21b, extending horizontally in the Y axis direction, are integrally provided on either side with respect to the X axis direction of the bottom section 21a of the base platform 21. A portion of each of the shelf sections 21b projects toward the center side along the X axis direction. Y axis rails 26, 27 are provided on the upper surfaces of the shelf sections 21b such that the Y axis rails 26, 27 oppose the respective gate sections 22, 23. A substrate table 60, which is described below, is mounted on the Y axis rails 26, 27. The substrate table 60 is configured to be reciprocally movable back and forth along the Y axis rails 26, 27.

Each of the gate sections 22, 23 is formed in a gate shape spanning the corresponding substrate carry-in port 11d or carry-out port 11e of the housing 11. Each of the gate sections 22, 23 has a built-in shutter mechanism which is installed in the corresponding walls 11b, 11c of the housing 11.

Each of the lower portions of the frame sections 24, 25 is welded to respective top portions of the corresponding gate sections 22, 23. Each of the upper surface sections of the frame sections 24, 25 is also welded to respective end sections of the beam 30 with respect to the X axis direction. The frame sections 24, 25 form a solid frame structure, together with the gate sections 22, 23 and the beam 30.

The beam 30 is a structure which supports the X-ray irradiation unit as an X-ray source, as described in detail below (see FIG. 7 to FIG. 9).

Figure 3:
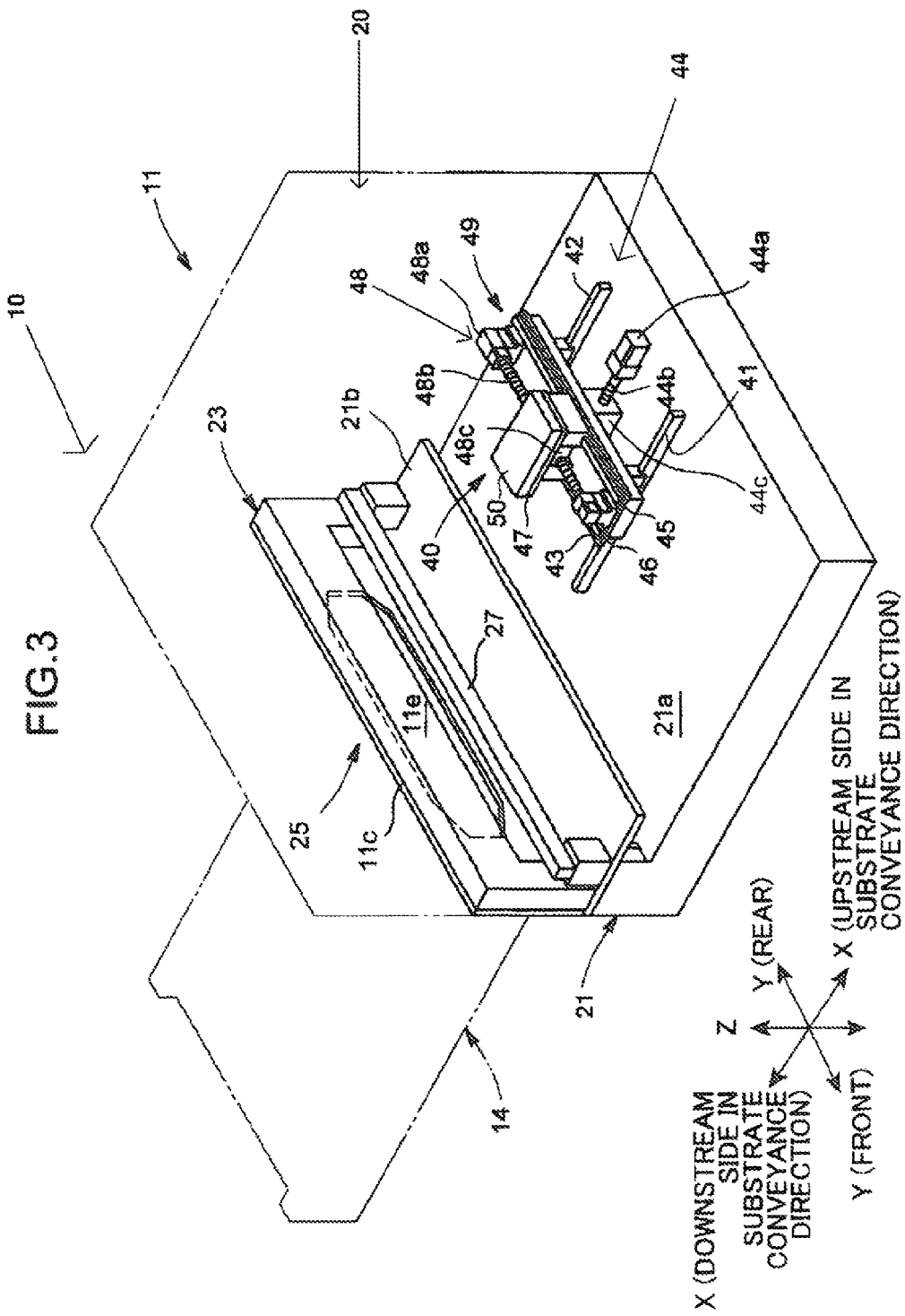
FIG. 3 is a perspective diagram showing a schematic configuration of an X-ray camera unit which is employed in the complex inspection device in FIG. 1.

Next, referring to FIG. 3, the X-ray camera unit 40 is provided with: a pair of X axis guide rails 41, 42 affixed to the bottom section 21a of the base platform 21, having a space with an interval along the Y axis direction, and respectively extending in the X axis direction; an X axis slide table 43 being guided on the X axis guide rails 41, 42 and configured to move in the X axis direction; an X axis ball screw mechanism 44 provided below the X axis slide table 43 and configured to drive the X axis slide table 43 along the X axis direction; a pair of Y axis guide rails 45, 46 fixed to the upper portion of the X axis slide table 43 and extending respectively along the Y axis direction; a Y axis slide table 47 being guided by the pair of Y axis guide rails 45, 46 and configured to move along the Y axis direction; a Y axis ball screw mechanism 48 provided below the Y axis slide table 47 and configured to drive the Y axis slide table 47 along the Y axis direction; and an X-ray camera 50 provided on top of the Y axis slide table 47.

The X axis guide rails 41, 42 are disposed slightly towards the rear side in the central portion of the bottom section 21a and, in this position, the X axis guide rails 41, 42 guide the X axis slide table 43 reciprocally along the X axis direction.

The X axis slide table 43 is formed in a rectangular shape in plan view and extending to a long dimension in the Y axis direction.

The X axis ball screw mechanism 44 is provided with an X axis motor 44a which is mounted on the bottom section 21a, a ball screw 44b which is driven to rotate by the X axis motor 44a, and a nut section 44c threadedly engaging with the ball screw 44b and being fixed to the bottom surface of the X axis slide table 43. The X axis slide table 43 is configured to reciprocally move along the X axis direction on the X axis guide rails 41, 42, in response to the nut section 44c moving along the X axis direction due to rotation of the ball screw 44b.

The Y axis guide rails 45, 46 extend along the Y axis direction substantially entire length of the X axis slide table 43, with an interval spaced apart in the width direction of the X axis slide table 43 (the X axis direction). These Y axis guide rails 45, 46 guide the Y axis slide table 47 so that the Y axis slide table 47 is reciprocally movable back and forth along the Y axis direction.

The Y axis slide table 47 is a rectangular member which is set to be slightly longer in the X axis direction when observed in plan view. An X-ray camera 50 is carried on the upper surface of the Y axis slide table 47. Consequently, the X-ray camera 50 is configured to be movable back and forth and left and right (X and Y axis directions) over the bottom section 21a, by movement of the X axis slide table 43 and the Y axis slide table 47. As being mounted on the Y axis slide table 47, the X-ray camera 50 projects slightly above the shelf sections 21b of the base platform 21.

The Y axis ball screw mechanism 48 is provided with an Y axis motor 48a which is mounted on a rear end portion of the X axis slide table 43, a ball screw 48b which is driven to rotate by the Y axis motor 48a, and a nut section 48c which threadedly engages with the ball screw 48b and is fixed to the bottom surface of the Y axis slide table 47. The Y axis slide table 47 is configured to be reciprocally movable along the Y axis direction on the Y axis guide rails 45, 46, in response to the nut section 48c moving along the Y axis direction due to rotation of the ball screw 48b. Namely, the X axis guide rails 41, 42, the X axis slide table 43, the X axis ball screw mechanism 44, the Y axis guide rails 45, 46, the Y axis slide table 47, and the Y axis ball screw mechanism 48 form X-ray camera movement means 49 which moves the X-ray camera 50 in both the X axis direction and the Y axis direction in a plane that is parallel to the printed substrate W.

Figure 4:
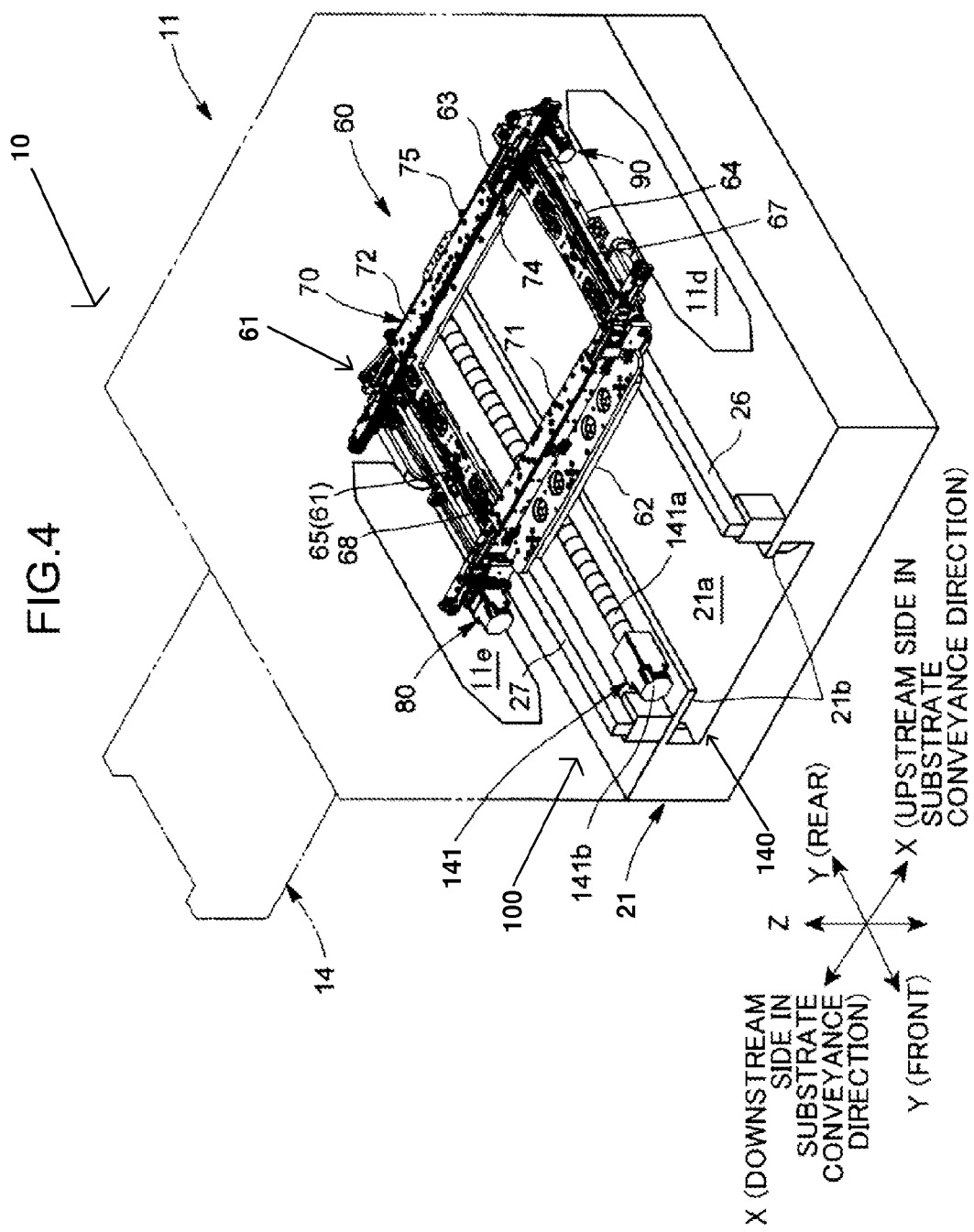
FIG. 4 is a perspective diagram showing a schematic configuration of a substrate table which is employed in the complex inspection device in FIG. 1.
Figure 5:
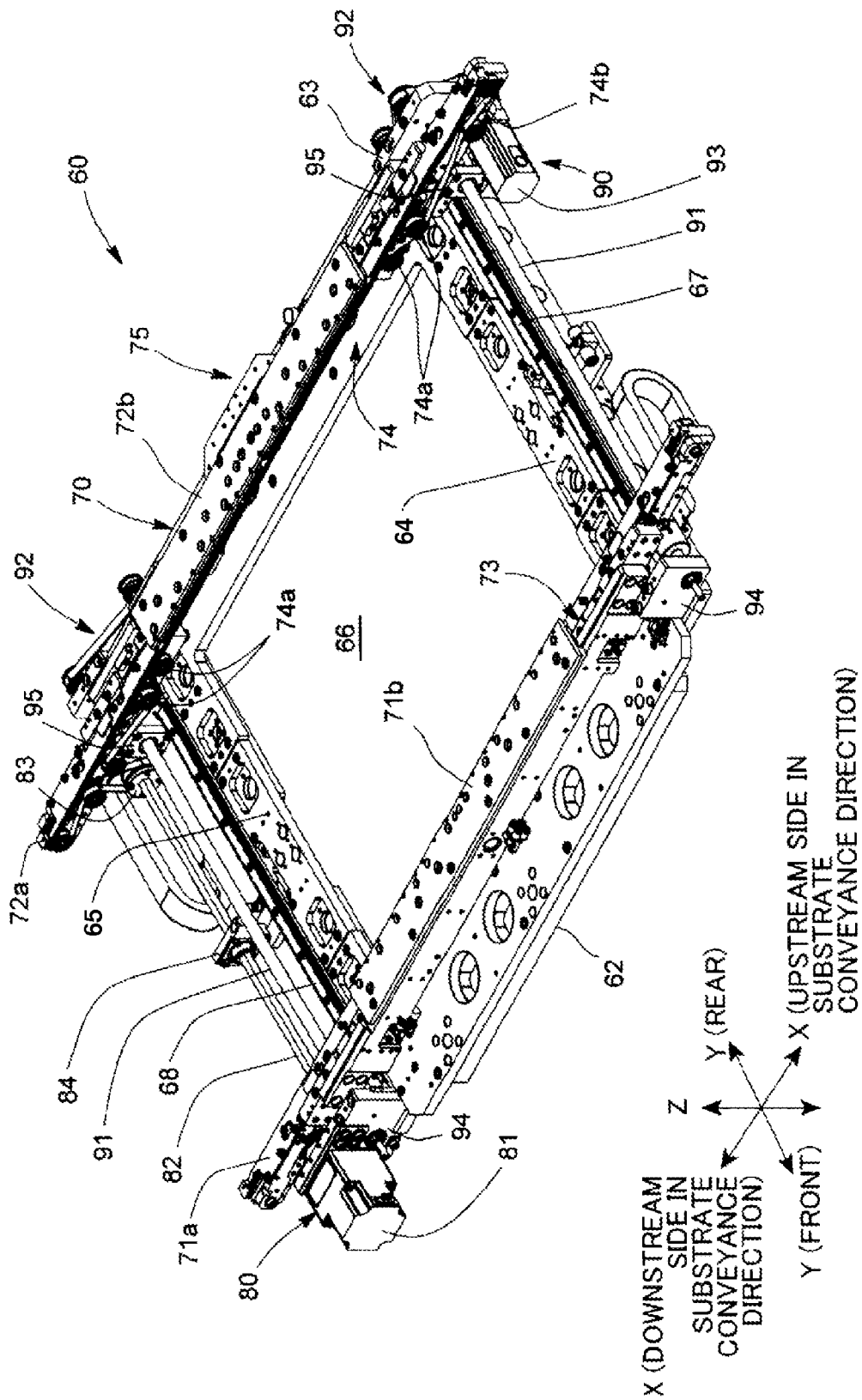
FIG. 5 is a perspective diagram showing an enlarged view of the substrate table in FIG. 4.
Figure 6:
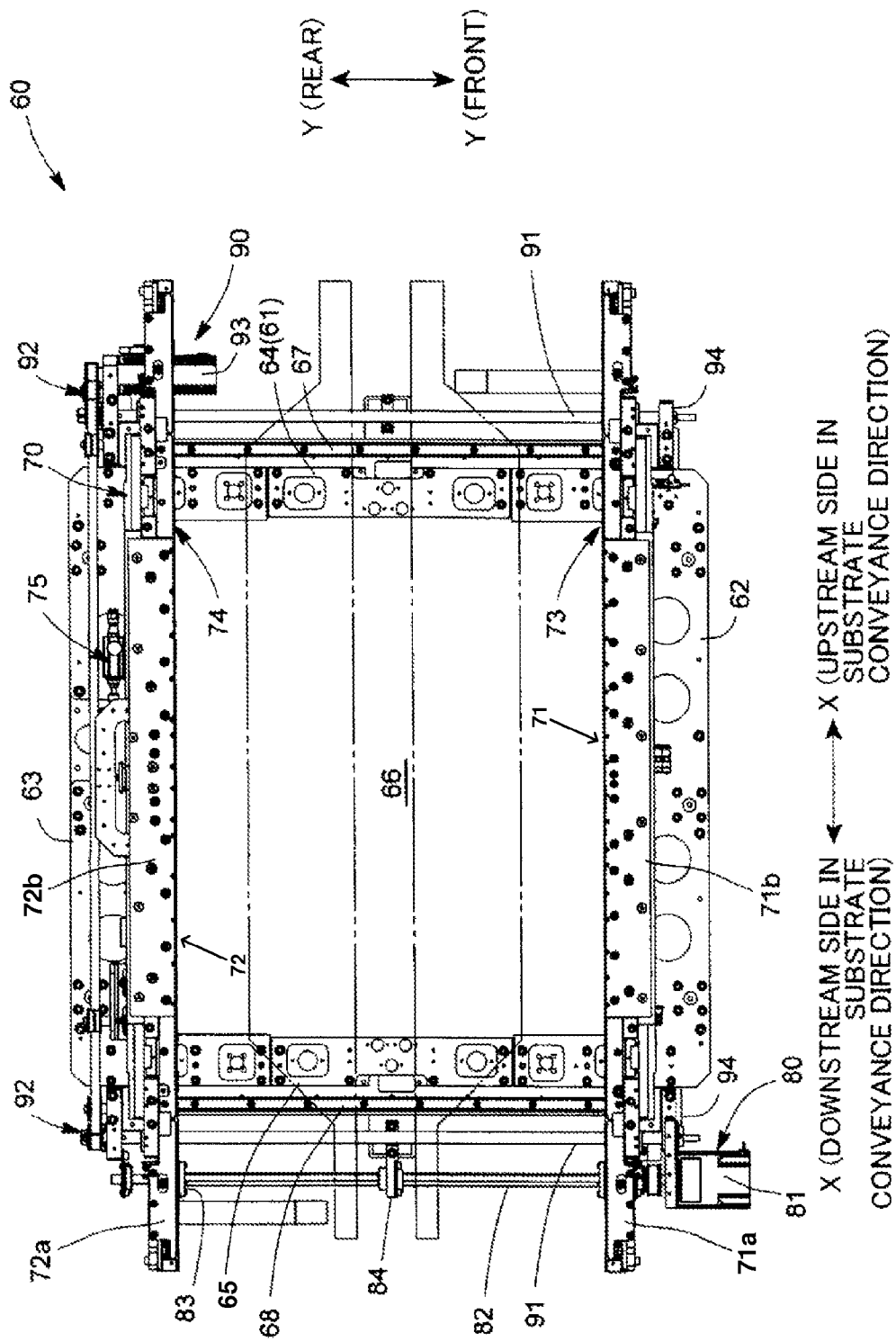
FIG. 6 is a plan diagram of the substrate table in FIG. 4.

Next, referring to FIG. 4 to FIG. 6, the substrate table 60 is provided with: a frame body 61 forming a main body portion; a conveyor unit 70 which conveys and holds the printed substrate W on the frame body 61; a conveyor drive mechanism 80 which drives substrate conveyance conveyors 73, 74 provided on the conveyor unit 70; and an interval adjusting mechanism 90 which changes the opposition interval of the conveyor unit 70. Furthermore, the complex inspection device 10 relating to the present embodiment is provided with a table-driving mechanism 100 for driving the substrate table 60 in the X axis direction and the Y axis direction (see FIG. 4, FIG. 7 and FIG. 8).

The frame body 61 is coupled to the table-driving mechanism 100 which is described below. The frame body 61 is disposed movably in the X and Y axis directions. As shown in the drawings, the frame body 61 is formed in a rectangle frame shape in which a pair of X axis pieces 62, 63 extending in the X axis direction and a pair of Y axis pieces 64, 65 provided in either end portion of the X axis pieces 62, 63 extending in the Y axis direction are integrally provided, so that an opening 66 which transmits X-rays is formed in a central portion of the frame body 61.

Y axis rails 67, 68 are respectively fixed to the upper surfaces of the Y axis pieces 64, 65 of the frame body 61. The conveyor unit 70 is mounted on the Y axis rails 67, 68, and the conveyor unit 70 is movably formed along the Y axis direction on the Y axis rails 67, 68.

The conveyor unit 70 is provided with a pair of frame bodies 71, 72 which are disposed on front and rear positions with respect to the Y axis direction, substrate conveyance conveyors 73, 74 which are provided on the frame bodies 71, 72, and a clamp unit 75 which is provided on one of the frame bodies (a frame body disposed on the rear side in the Y axis direction in the example in the drawings) 72.

The frame bodies 71, 72 are provided with X axis frames 71a, 72a which extend respectively in the X axis direction and have an end portion projecting from the frame body 61, and regulating plates 71b, 72b which are disposed on the upper surfaces of the X axis frames 71a, 72a and have side portions which project towards the opening 66 side. To convey printed substrates W of various widths, the frame bodies 71, 72 are configured to change distance between the X axis frames 71a, 72a by moving the X axis frames respectively along the Y axis direction in accordance with the width of the printed substrate W, by means of the interval adjustment mechanism 90 which is described below. Furthermore, the regulating plates 71b, 72b are configured to be driven up and down by the clamp unit 75.

The substrate conveyance conveyors 73, 74 are formed by a plurality of rollers 74a disposed on the surfaces where the frame bodies 71, 72 face each other, and a belt 74b which is wound about the rollers 74a. In FIG. 5, although the rollers and belt of the substrate conveyance conveyor 73 on the front side are concealed, the configurations thereof are set to the same specifications as the rollers 74a and belt 74b of the substrate conveyance conveyor 74 on the rear side.

The clamp unit 75 has an air cylinder (not illustrated) which advances and retracts a rod in the Z axis direction, and a drive force transmission mechanism (not illustrated) which moves up and down the regulating plates 71b, 72b by advancement and retraction of the rod of the air cylinder. The regulating plates 71b, 72b are moved up and down by the drive force of the air cylinder, such that the respective end portions of the printed substrate W in the Y direction are respectively gripped and vertically held by the regulating plates 71b, 72b of the frame bodies 71, 72, and the belts of the substrate conveyance conveyors 74 (only the belt 74b is depicted in the drawings).

The conveyor drive mechanism 80 is provided with: a motor 81 mounted on one end portion in the X axis direction on the front side of the frame body 61, and outputting drive force about the Y axis; a drive shaft 82 being disposed along the Y axis direction on the downstream side in terms of the X axis direction between the two substrate conveyance conveyors 73, 74, and being driven to rotate about the Y axis by the motor 81; and output pulleys 83 (only the pulley for the substrate conveyance conveyor 74 is depicted in the drawings) provided respectively for each of the substrate conveyance conveyors 73, 74 being coupled to the drive shaft 82, and configured to output drive force to the belt 74b of the corresponding substrate conveyance conveyor 73, 74. The drive shaft 82, which is driven by the motor 81, is formed with a polygonal cross-section which restricts relative rotation with respect to the drive shaft 82. In this state, the respective output pulleys 83 are coupled so that each of the output pulleys 83 is relatively movable along the Y axis direction with respect to the drive shaft 82. In the example shown in the drawings, the drive shaft 82 is smoothly, rotatably, supported by a bearing 84 which is mounted on the Y axis piece 65 of the frame body 61.

The interval adjusting mechanism 90 is provided with: dual screw bolts 91 disposed respectively on both sides of the X axis direction of the two frame bodies 71, 72, and extending respectively along the Y axis direction; drive force transmission units 92 provided on the rear surface of the rear side frame body 72, and configured to transmit rotational force in the same direction to both of the dual screw bolts 91; and a motor 93 mounted on the other end side of the rear side frame body 72 with respect to the X axis direction, and configured to output rotational force about the Y axis to the drive force transmission unit 92. Each of the dual screw bolts 91 is formed with a right thread and a left thread symmetrically with a center with respect to the Y axis direction. Each of the dual screw bolts 91 is threadedly engaged with respective nut mechanisms 94, 95 which are mounted on the frame bodies 71, 72. The dual screw bolts 91 are configured to drive the frame bodies 71, 72 in a reciprocal manner: when they are rotated in one direction (for example, a clockwise direction), the dual screw bolts 91 act conjointly with the nut mechanisms 94, 95, and pull the two frame bodies 71, 72 together in a mutually approaching direction as shown by the virtual lines in FIG. 6; and when they are rotated in the other direction (for example, a counter-clockwise direction), the dual screw bolts 91 move the two frame bodies 71, 72 apart in a mutually separating direction, as indicated by the solid line in FIG. 6.

Figure 7:
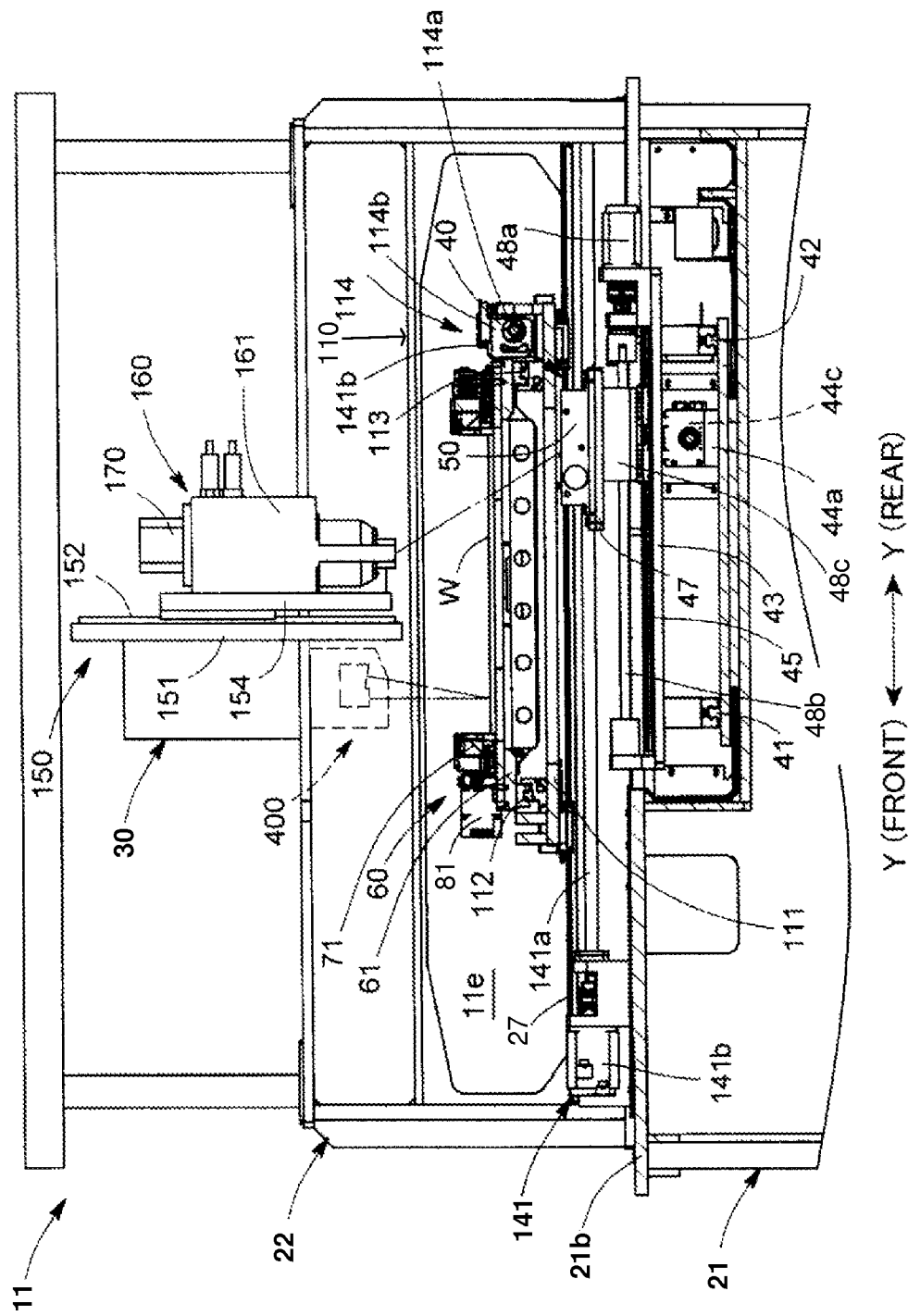
FIG. 7 is a cross-sectional diagram showing a downstream side in the substrate conveyance direction of the complex inspection device in FIG. 1.

Next, referring to FIG. 7, the table-driving mechanism 100 is provided with an X axis drive unit 110 which drives the substrate table 60 along the X axis direction, and a Y axis drive unit 140 (see FIG. 4) which drives the substrate table 60 in the Y axis direction via the X axis drive unit 110.

The X axis drive unit 110 is provided with a movable frame 111 disposed on the lower surface of the frame body 61 of the substrate table 60, a pair of X axis rails 112, 113 disposed on the movable frame 111 with intervals spaced apart in the Y axis direction and configured to guide the substrate table 60 along the X axis direction, and an X axis ball screw mechanism 114 provided in parallel on the rear side of the rear X axis rail 113. Similarly to the frame body 61, the movable frame 111 is a frame-shaped structure having an opening at the center. The X axis ball screw mechanism 114 is provided with a ball screw 114a extending along the X axis direction, a nut section (not illustrated) threadedly engaging with the ball screw 114a, and an X axis motor 114b configured to drive the ball screw 114a about the X axis. The nut section is fixed to the frame body 61 of the substrate table 60. The nut section is configured to receive the rotational force of the ball screw 114a, and to transmit force for moving the substrate table 60 in the X axis direction relatively with respect to the movable frame 111. Consequently, when the X axis motor 114b rotates and the ball screw 114a rotates, the substrate table 60 receives force in the X axis direction from the nut section and can be moved reciprocally in the X axis direction.

Referring to FIG. 4, the Y axis drive unit 140 is provided with the pair of Y axis rails 26, 27 which are provided on the shelf sections 21b, and a Y axis ball screw mechanism 141 which is provided in parallel with an inner side of the Y axis rail 27 on the downstream side (on the side in the X axis direction which opposes the Y axis rail 26 on the upstream side in the substrate conveyance direction) with respect to the substrate conveyance direction. The Y axis rails 26, 27 respectively guide the movable frame 111 such that the movable frame 111 is reciprocally movable in the Y axis direction. The Y axis ball screw mechanism 141 is provided with a ball screw 141a extending along the Y axis direction, a nut section (not illustrated) which threadedly engages with the ball screw 141a, and a Y axis motor 141b which drives the ball screw 141a to rotate. The ball screw 141a is rotatably supported on the shelf sections 21b by bearings, which are not illustrated. The nut section is fixed to the lower surface of the movable frame 111 so as to receive rotational force from the ball screw 141a, and to transmit force for driving the substrate table 60 in the Y axis direction via the movable frame 111. The Y axis motor 141b is fixed at an appropriate position to the shelf sections 21b. The substrate table 60 is configured to receive force in the Y axis direction from the nut section and to enable reciprocally moving in the Y axis direction, when the Y axis motor 141b rotates and the ball screw 141a rotates.

Next, the X-ray irradiation unit (one example of an X-ray source) 160 for carrying out transmissive inspection of a printed substrate W held on the substrate table 60 will be described. The X-ray irradiation unit 160 is carried on an X-ray source supporting mechanism 150, which is one example of magnification changing means (lifting apparatus) that is configured to enable changing the magnification of the X-ray image by lifting the X-ray source. Therefore, this X-ray source supporting mechanism 150 will be described first.

Figure 8:
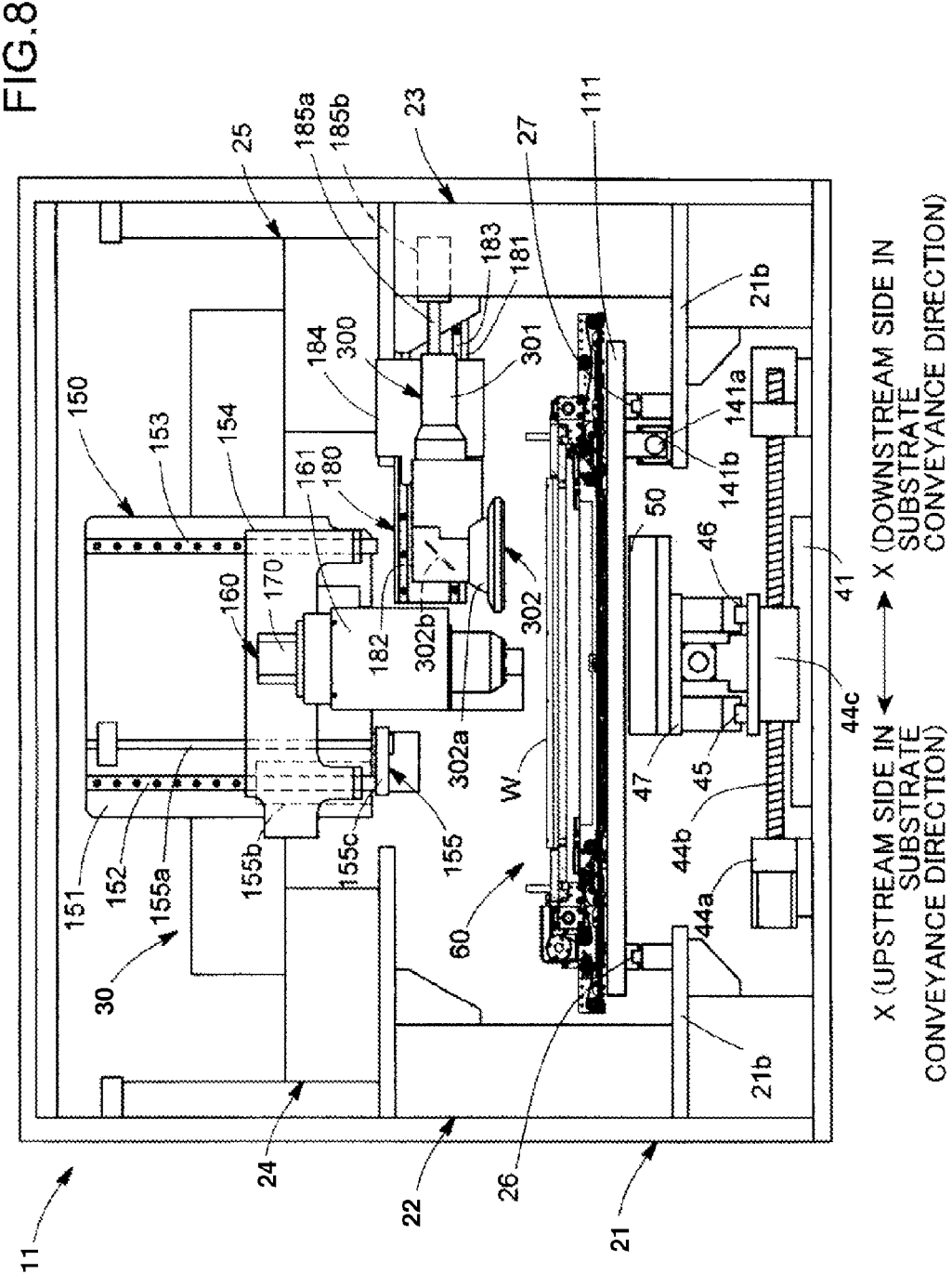
FIG. 8 is a cross-sectional diagram showing a rear surface side of the complex inspection device in FIG. 1.
Figure 9:
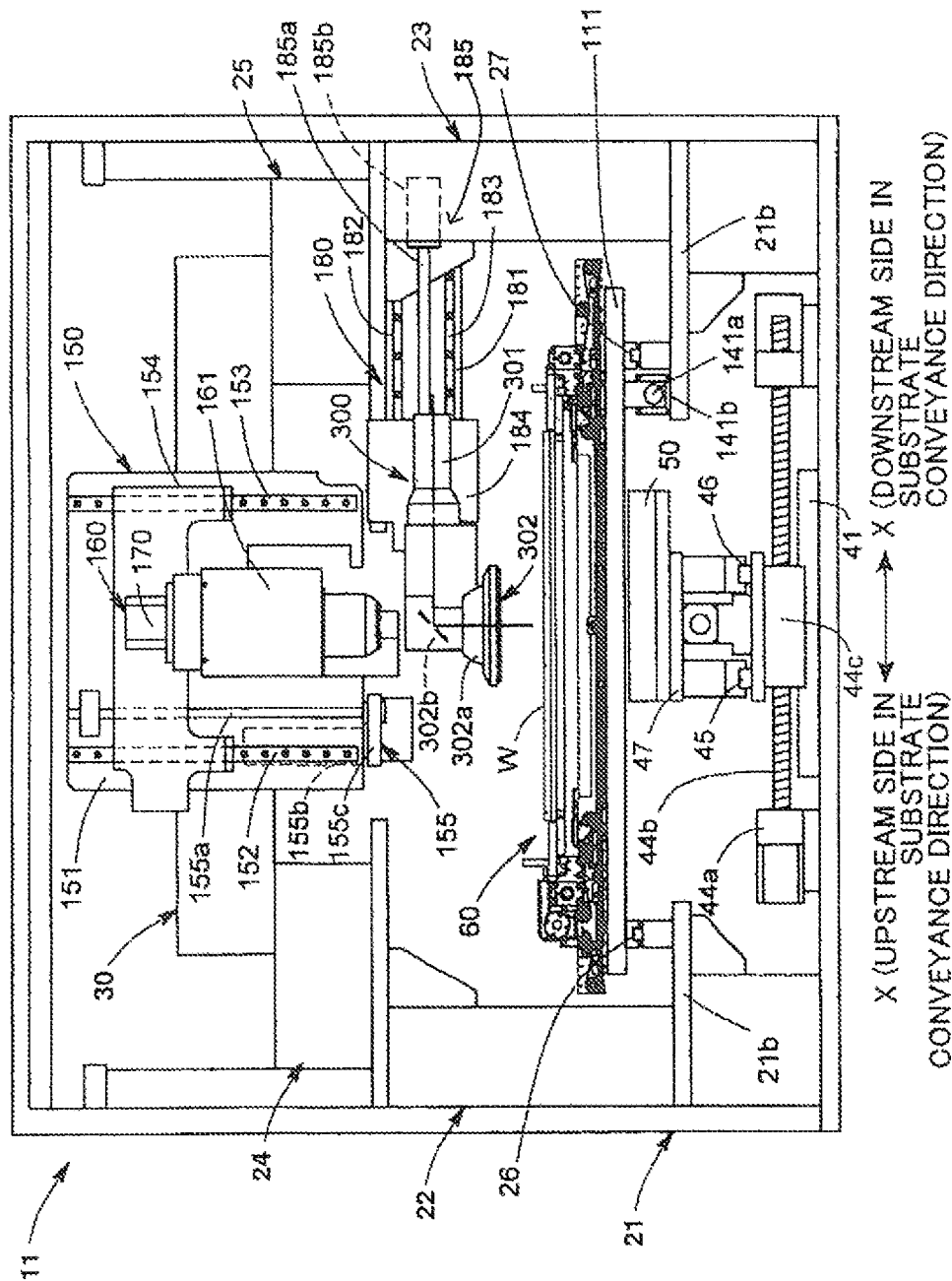
FIG. 9 is a cross-sectional diagram showing a rear surface side of the complex inspection device in FIG. 1.

Referring to FIG. 8 and FIG. 9, the X-ray source supporting mechanism 150 is provided with a plate-shaped support plate 151 which is fixed to a rear surface of the beam 30, a pair of vertical rails 152, 153 fixed to a rear surface of the support plate 151 and extending along the Z axis direction, a slider 154 which is coupled to the vertical rails 152, 153, and a ball screw mechanism 155 which drives the slider 154 upwards and downwards. The support plate 151 is a metallic plate forming the structure 20 together with the beam 30. In the example illustrated, the support plate 151 is fixed securely to the beam 30. Stoppers (not illustrated) are provided on the support plate 151 so that the slider 154 is guided vertically moving in the Z axis direction within a stroke range that is defined by the stoppers. The stroke range is determined on the basis of the desired magnification required in the X-ray images from the complex inspection device 10.

Figure 15B:
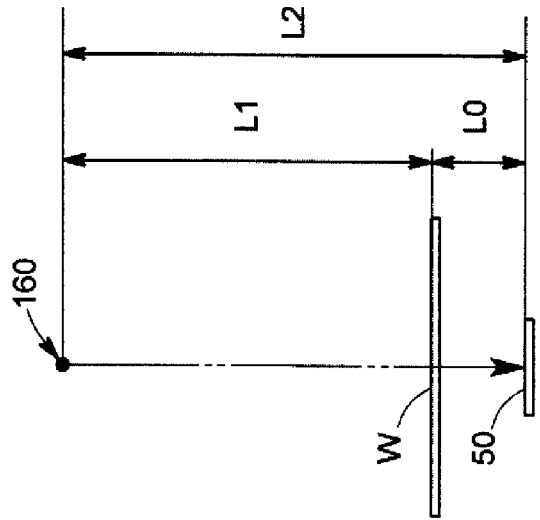
FIG. 15B is an illustrative diagram showing an arrival path at a non-close-up position with respect to change in the magnification of an X-ray image from an X-ray camera unit which is employed in the complex inspection device in FIG. 1.
Figure 15A:
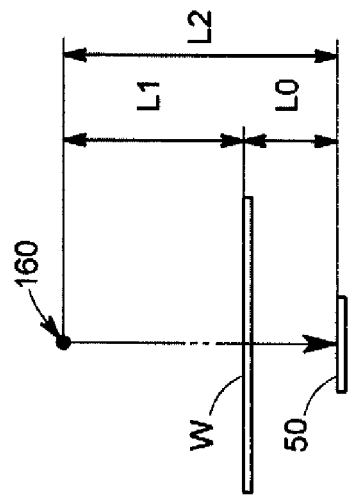
FIG. 15A is an illustrative diagram showing an arrival path at a close-up position with respect to change in the magnification of an X-ray image from an X-ray camera unit which is employed in the complex inspection device in FIG. 1.

The slider 154 directly supports the X-ray irradiation unit 160. Referring to FIG. 15A and FIG. 15B, when this slider 154 moves upwards or downwards along the vertical rails 152, 153, distance L1 is changed. The distance L1 is defined from the X-ray irradiation unit 160 as a point-shaped X-ray source or a point X-ray source, as shown in FIG. 15A and FIG. 15B, to the printed substrate W held on the substrate table 60a. This causes distance L2 to change, even if distance L0 is uniform. The distance L0 is defined as a distance from the printed substrate W to the X-ray camera unit 40. The distance L2 (=L0+L1) is defined as a distance of arrival path along which the X-lay is transmitted from the X-ray irradiation unit 160 through the printed substrate W to the X-ray camera unit 40. When the distances L1 and L2 are changed, the magnification L2/L1 (=1+(L0/L1)) of the X-ray image captured by the X-ray camera unit 40 is also changed. As shown in FIG. 8 and FIG. 15A, when the X-ray irradiation unit 160 is lowered, the arrival path is referred to as a first distance and the magnification of the X-ray image is a close-up magnification where an image is elongated larger than same-size magnification. Namely, when the X-ray irradiation unit 160 is lowered, it takes a close-up position. Furthermore, as shown in FIG. 9 and FIG. 15B, when the X-ray irradiation unit 160 is raised, the arrival path is changed to a second distance which is longer than the first distance. The image has a non-close-up magnification which is a lower magnification and has a broader angle than when imaging in the close-up position (a magnification greater than same-size). Namely, when the X-ray irradiation unit 160 is raised, it takes a non-close-up position. The vertical rails 152, 153 guide the slider 154 such that the X-ray irradiation unit 160 is moved up and down between the close-up position and the non-close-up position.

Furthermore, the complex inspection device 10 according to the present embodiment is configured to irradiate X-rays at a prescribed elevation angle (for example, 45°) measured form the printed substrate W, and to carry out oblique imaging to capture images of the inspection object portion from an oblique angle. In this oblique imaging, constraint is established in a control unit 600, which is described hereinafter, so that the close-up position is mandatory to be taken whenever the oblique imaging is carried out.

The ball screw mechanism 155 is provided with a ball screw 155a extending in the Z axis direction and being supported axially on a rear surface of the support plate 151, a nut section (not illustrated) threadedly engaging with the ball screw 155a, a Z axis motor 155b configured to drive the ball screw 155a to rotate about the Z axis, and a belt mechanism 155c configured to transmit the output of the Z axis motor 155b to the ball screw 155a. The ball screw 155a extends through substantially the entire height of the support plate 151, allowing the X-ray irradiation unit 160 to be moved up and down within the stroke range. The nut section (not illustrated) is fixed to a front surface of the slider 154. The nut section is configured to receive rotational force from the ball screw 155a, and thereby transmitting force for moving the slider 154 in the upward and downward directions. The Z axis motor 155b is mounted on a front surface of the support plate 151 with the output shaft thereof facing downwards along the Z axis direction. The belt mechanism 155c includes an output pulley mounted on an output shaft of the Z axis motor 155b, an input pulley mounted on a lower end of the ball screw 155a, and a belt wound between these pulleys. The belt mechanism 155c is configured to transmit drive power from the Z axis motor 155b to the ball screw 155a via the pulleys and the belt. In this way, the X-ray source supporting mechanism 150 including the Z axis ball screw mechanism 155 forms magnification changing means, or a lifting apparatus, which changes the magnification of the X-ray image, and more specifically by displacing the X-ray irradiation unit 160 between a close-up position (see FIG. 8) where the linear distance of X-rays irradiated from the X-ray irradiation unit 160 to the X-ray camera 50 is set in a short distance for close-up imaging, and a non-close-up position (see FIG. 9) where the linear distance of X-rays irradiated from the X-ray irradiation unit 160 to the X-ray camera 50 is set longer than the distance in the close-up position.

Next, in the example shown in the drawings, the X-ray irradiation unit 160 is provided with a housing 161, a high-voltage generating unit (not illustrated) which is accommodated inside this housing, and an X-ray radiation apparatus 200 configured to irradiate X-rays upon receiving a supply of electric power from the high-voltage generating unit.

Figure 10:
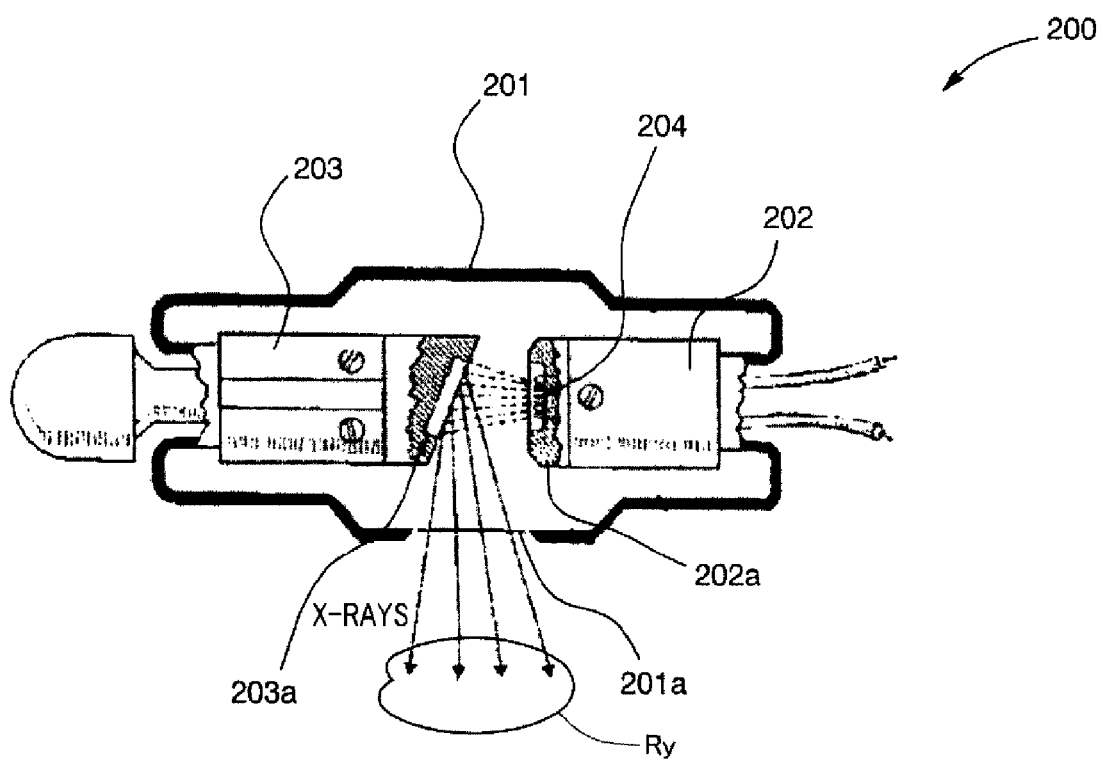
FIG. 10 is a schematic view showing one example of a configuration of an X-ray radiation apparatus which can be employed in the complex inspection device in FIG. 1.

Referring to FIG. 10, the X-ray radiation apparatus 200 is provided with a glass tube 201 having a radiation window 201a, a cathode 202 fixed to one end of the glass tube 201 and having a focusing cylinder 202a at the other end side of the glass tube 201, and an anode 203 fixed to the other end side of the glass tube 201 and having a target 203a opposing the focusing cylinder 202a of the cathode 202. A filament 204 is provided in the focusing cylinder 202a of the cathode 202, so as to face the target 203a on the anode 203. The target 203a is made from tungsten and is inclined through 45°, for example, with respect to the central line of the glass tube 201, thereby enabling X-rays radiated from the filament 204 to be radiated to the outside of the glass tube 201 via the radiation window 201a. Here, if thermal electrons were irradiated onto the inclined surface of the target 203a, X-rays would be distributed in an approximate heart shape, as shown by Ry in FIG. 10, with the location corresponding to the lower side of inclination of the target 203a being shaded, rather than being distributed in all direction angles. Therefore, the X-ray radiation apparatus 200, for example, of the X-ray irradiation unit 160 can be rotated about the Z axis, and hence irradiation of the X-rays which are distributed in an approximate heart shape can be rotated about the Z axis, whereby oblique irradiation can be guaranteed in a direction from the cathode 202 towards the anode 203 in FIG. 10 (for example, on the upstream side of the substrate conveyance direction shown in FIG. 9). Consequently, if the X-ray camera 50 of the X-ray camera unit 40 were moved in the leftward direction in FIG. 9, it would be possible to obtain an oblique X-ray image of the substrate W using X-rays which have been irradiated in a leftward and downward direction. The oblique X-ray image in this case is an image based on X-rays at an angle which intersects with the printed substrate W (a leftward elevation angle, since the X-rays enter from the top right and exit from the bottom left).

As shown in FIG. 8 and FIG. 9, in order to obtain oblique X-ray images at a prescribed plurality of elevation angles with respect to all directions in each location on the printed substrate W, the substrate table 60 is controlled to move in the X axis direction and the Y axis direction by the table-driving mechanism 100, the X-ray camera 50 is controlled to move in the X axis direction and the Y axis direction in the X-ray camera unit 40, and the X-ray radiation apparatus 200 of the X-ray irradiation unit 160 is rotated about the Z axis by operation of an R axis motor 170. The R axis motor 170 is rotation-controlled by the control unit 600, which is described below.

Next, an optical imaging apparatus 300 which is provided in parallel with the X-ray irradiation unit 160 will be described. The optical imaging apparatus 300 is carried on the optical drive mechanism 180, which serves as optical system drive means. Therefore, this optical drive mechanism 180 will be described first.

The optical drive mechanism 180 is provided with a guide frame 181 provided directly below a frame unit 25 that supports one end of the beam 30 and extending in the X axis direction, a pair of guide rails 182, 183 which are disposed on the rear surface of the guide frame 181 with spaces apart in the Z axis direction, the pair of guide rails 182, 183 respectively extending in parallel along the X axis direction, a slider 184 coupled to the guide rails 182, 183 and being supported movably in the X axis direction, and a ball screw mechanism 185 provided between the slider 184 and the guide frame 181. The guide frame 181 is a metallic plate member which forms apart of the structure 20, together with the beam 30 and the frame section 25. Stoppers (not illustrated) are provided on the support plate 181, and the slider 184 is reciprocally movably guided in the X axis direction, within a stroke range that is restricted by the stoppers. In this stroke range, the guide rails 182, 183 guide the slider 184 in a way that the optical imaging apparatus 300 is movable between an imaging position as shown in FIG. 9, where, when the X-ray irradiation unit 160 is in the non-close-up position, the optical imaging apparatus 300 faces directly below the X-ray irradiation unit 160 so that the optical imaging apparatus 300 enables imaging based on visible light, and a withdrawn position as shown in FIG. 8, where the optical imaging apparatus 300 is moved out in the X axis direction from the imaging position so that the X-ray irradiation unit 160 is allowed to descend from the non-close-up position to the close-up position. The ball screw mechanism 185 is provided with a ball screw 185a extending in the X axis direction and being pivotably supported on the rear surface of the guide frame 181, a nut section (not illustrated) threadedly engaging with the ball screw 185a, and an X axis motor 185b configured to drive the ball screw 185a to rotate about the X axis. The ball screw 185a extends through substantially the whole length of the guide frame 181 so that the optical imaging apparatus 300 enables moving in the stroke range described above. The nut section is fixed to a front surface of the slider 184, and configured to receive rotational force from the ball screw 185a, thereby transmitting force for moving the slider 184 along the X axis direction. The X axis motor 185b is installed at a suitable position on the structure 20, in a state where an output shaft thereof is aligned with the X axis direction. The X axis motor 185b is thus configured to transmit the drive force of the X axis motor 185b to the ball screw 185a. In this way, the optical drive mechanism 180 forms drive means configured to move the optical imaging apparatus 300 between an imaging position (see FIG. 9) where the optical imaging apparatus 300 faces the inspection object portion between the X-ray irradiation unit 160 and the X-ray camera 50, and a withdrawn position (see FIG. 8) where the optical imaging apparatus 300 is moved out from the imaging position so that the X-ray irradiation unit 160 and the X-ray camera 50 are allowed to relatively move toward the close-up position.

Next, the optical imaging apparatus 300 is provided with a CCD camera 301 carried on the slider 184, and an optical system 302 is formed as a unit with the CCD camera 301 and facing the top of the substrate table 60. The CCD camera 301 is configured to receive light from the optical system 302 by directing a lens (not illustrated) along the X axis direction. The optical system 302 is provided with an annular-shaped hood 302a, and a mirror 302b disposed above the hood 302a and inclining at 45° so as to face the side portion of the CCD camera 301. A plurality of LEDs is provided inside the hood 302a. The plurality of LEDs is configured to irradiate downwardly. Furthermore, a through hole is formed in a central portion of the hood 302a, so that the hood 302a is configured to transmit X-rays and reflected light from the inspection object portion of the printed substrate W through the through hole. While being configured to transmit X-rays, the mirror 302b is configured to reflect further the reflected light from the inspection object portion of the printed substrate W below the hood 302a along the X axis direction, thereby directing this reflected light towards the CCD camera 301. In the present embodiment, the hood 302a having a through hole at the central portion and the mirror 302b are one example of a light receiving unit which forms the optical imaging apparatus that allows transmitting X-rays. In the embodiment depicted in the drawings, if the optical imaging apparatus 300 is in the imaging position, then the center of the mirror is set so that the center is positioned directly below the X-ray irradiation unit 160. Therefore, when the X-ray irradiation unit 160 irradiates X-rays in order to inspect the inspection object portion directly below, it is also possible to simultaneously capture images of the inspection object portion at the same position, in parallel with this irradiation operation. Capture of X-ray images based on X-rays from perpendicularly above the printed substrate W produced by the X-ray irradiation unit 160 in the non-close-up position, and capture of images based on visible light from perpendicularly above via the mirror 302b are carried out on each location of the printed substrate W. For this purpose, the substrate table 60 is controlled to move in the X axis direction and the Y axis direction by the table-driving mechanism 100, for each image capturing action.

Moreover, referring to FIG. 7, a laser inspection device 400 is disposed in front of the X-ray irradiation unit 160. The laser inspection device 400 is disposed at a position facing the printed substrate W on the substrate table 60, from a position near to the X-ray irradiation unit 160. Furthermore, the laser inspection device 400 is provided with an irradiation unit configured to irradiate a laser downwards, and a light receiving unit configured to receive laser light reflected from the inspection object portion. The laser inspection device 400 thus serves to detect the height of the inspection object portion on the basis of the light received by the light receiving unit. This height detection is simultaneously carried out with X-ray imaging and optical imaging, or independently from the same, in each of the prescribed locations on the printed substrate W. To attain this, the substrate 60 is controlled by the table-driving mechanism 100 to be moved in the X axis direction and the Y axis direction so as to be positioned for each height detection operation.

Next, referring to FIG. 1, a control unit 600 for controlling whole elements is equipped with the complex inspection device 10. The control unit 600 is one example of: imaging position control means configured to control the optical drive mechanism 180 so that, where it is necessary to move the X-ray irradiation unit 160 towards the close-up position, the optical imaging apparatus 300 is moved out in advance to the withdrawn position; table movement control means configured to control movement of the substrate table 60 in the X axis direction and the Y axis direction by the table-driving mechanism 100; and X-ray radiation apparatus rotation control means configured to control rotation of the X-ray radiation apparatus 200 about the Z axis (up/down axis) by the R axis motor 17, in order to obtain oblique X-ray images at a prescribed plurality of elevation angles in prescribed direction angles, in a case where the optical imaging apparatus 300 is moved out to a withdrawn position. In a case where the optical imaging apparatus 300 is moved out to the withdrawn position, the X-ray irradiation unit 160 takes the close-up position. Within the close-up position, the X-ray irradiation unit 160 is controlled to a height position matching the desired close-up magnification. For prescribed locations on the printed substrate W, capture of close-up X-ray images based on X-rays from perpendicularly above the printed substrate W and capture of oblique X-ray images based on X-rays at a prescribed direction angle and a prescribed elevation angle with respect to the printed substrate W will be carried out by altering the position of the substrate table 60, the position of the X-ray camera 50, and the Z axis rotation position of the X-ray radiation apparatus 200. In the present embodiment, a display panel 610 and a keyboard 620 are installed on the front surface of the complex inspection device 10. Furthermore, a lamp 611 indicating the operational status is provided at the top of the complex inspection device 10. Moreover, a power supply apparatus 630 is provided on the upstream side of the control unit 600 in the substrate conveyance direction.

Figure 11:
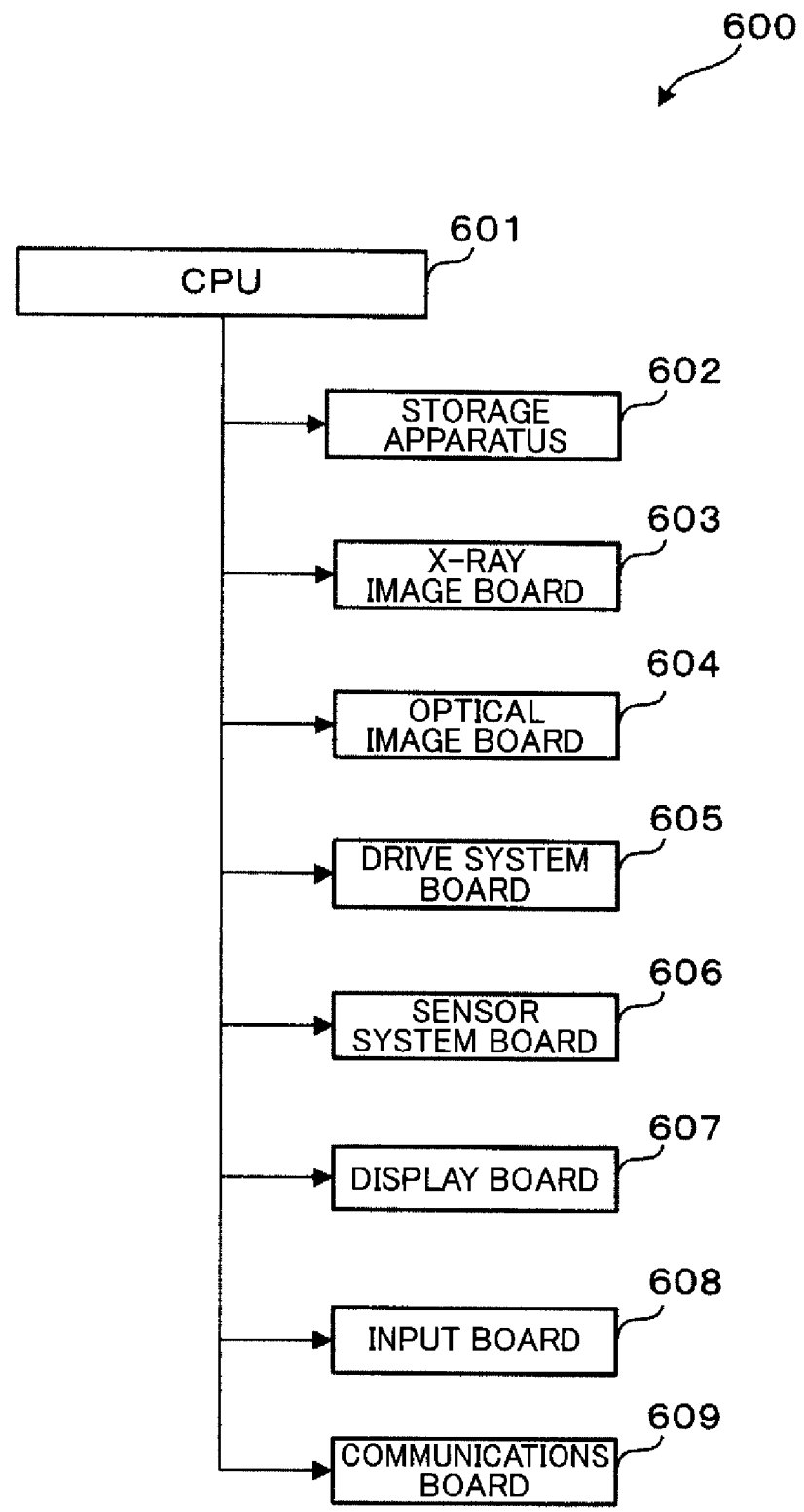
FIG. 11 is a block diagram showing a control unit of the complex inspection device in FIG. 1.

Referring to FIG. 11, the control unit 600 is provided with a main control unit (CPU) 601 which is realized by a microprocessor, or the like. A storage apparatus 602, an X-ray image board 603, an optical image board 604, a drive system board 605, a sensor system board 606, a display board 607, an input board 608, a communications board 609, and the like are connected to this main control unit 601.

The storage apparatus 602 is realized by a ROM, a RAM and an auxiliary storage device. The storage apparatus 602 stores programs and master data required to control the respective parts of the complex inspection device 10 and to carry out inspection, master data for inspection object products, such as the printed substrate W or an inspection object, the mounted components, the inspection items, and the like, and transaction data which specifies the inspection specifications in respect of the inspection object items, and so on.

The X-ray image board 603 is an interface for connecting the X-ray camera 50 and the main control unit 601. Through this X-ray image board 603, the main control unit 601 enables carrying out transmissive inspection of an inspection object product on the basis of X-ray images captured by the X-ray camera 50.

The optical image board 604 is an interface for connecting the CCD camera 301 and the main control unit 601. Through this optical image board 604, the main control unit 601 enables executing external inspection of the inspection object product on the basis of optical images captured by the CCD camera 301.

The drive system board 605 is an interface for connecting various motors provided in the complex inspection device 10

(for example, the X axis motors 44*a*, 141*b*, 114*b*, 144*b*, 155*b*, 185*b*, and so on, of the ball screw mechanisms 44, 114, 141, 155, 185), the actuators, and the like, of the clamp unit 75, and the main control unit 601. Through this drive system board 605, the main control unit 601 enables controlling the direction of rotation, amount of rotation, rotational speed, operation timing, and the like, of the various motors, or to control the opening and closing operations of the air cylinder of the clamp unit 75.

The sensor system board 606 is an interface which connects the various sensors provided in the complex inspection device 10 and the main control unit 601. Through this sensor system board 606, the main control unit 601 enables detecting the operation timing of the respective parts, and the presence or absence of the printed substrate W, and the like, on the basis of the detection results from the various sensors.

The display board 607 is an interface which connects the display panel 610 mounted on the front surface of the complex inspection device 10, the lamp 611 and the main control unit 601. Through this display board 607, the main control unit 601 enables displaying control information on the display panel 610 via a graphical user interface (GUI) or causes the lamp 611 provided on the top of the complex inspection device 10 to flash on and off (see FIG. 1).

The input board 608 is an interface which connects a pointing device such as a keyboard 620 or the like mounted on the front surface of the complex inspection device 10, with the main control unit 601. Through this input board 608, the main control unit 601 enables receiving data from the keyboard 620, or the like, which is operated by the user.

The communications board 609 serves to execute data communications with a host computer which manages a production program of the equipment in which the complex inspection device 10 is installed. Through this communications board 609, the main control unit 601 is connected to a host computer by LAN and/or WAN, so as to obtain information relating to inspection object items, such as the part number of the printed substrate W, or an inspection object.

The main control unit 601 controls the respective parts of the complex inspection device 10 by the following procedure, on the basis of a program, and the like, stored in the storage device 602.

Figure 12:
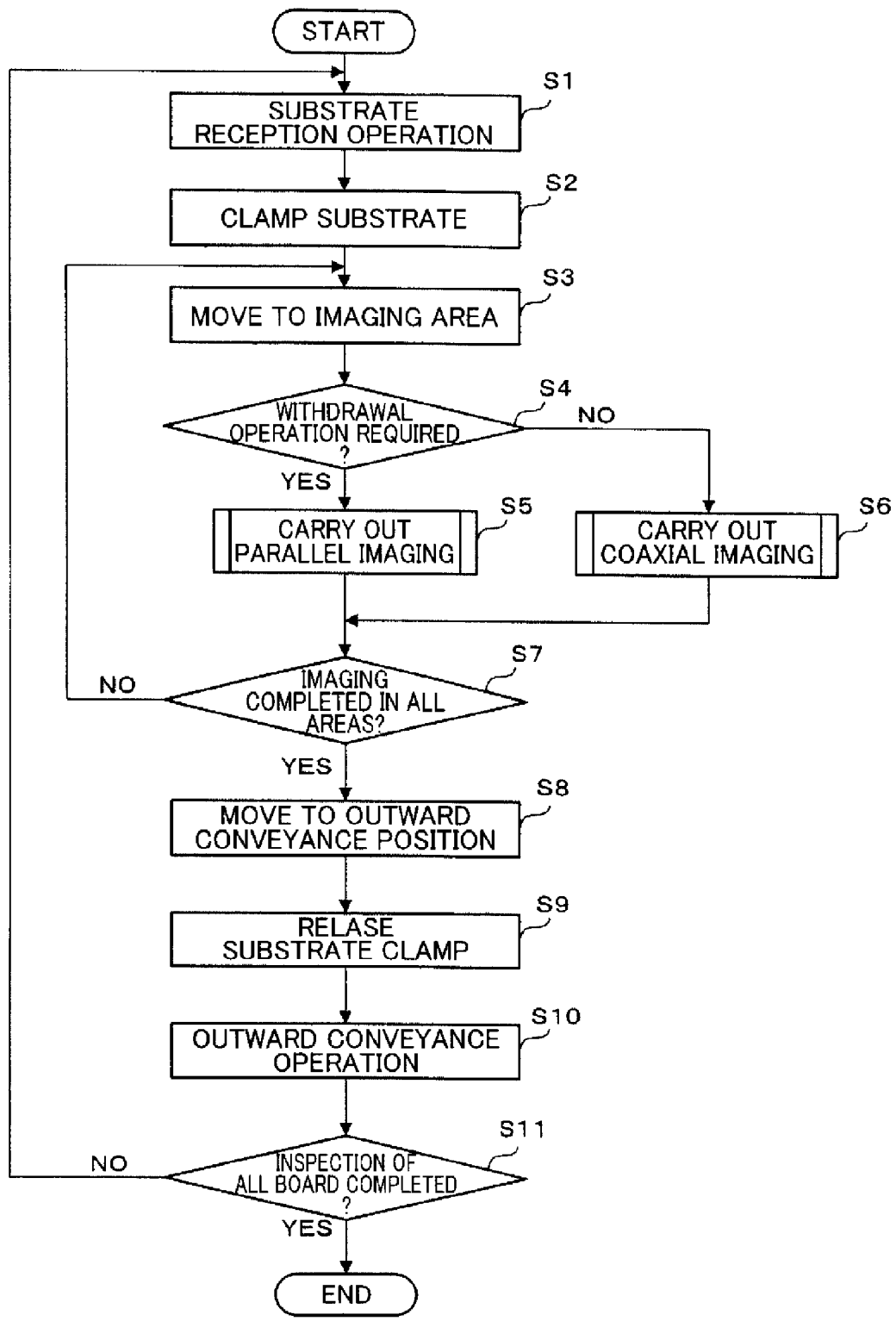
FIG. 12 is a flowchart showing an inspection operation of the complex inspection device in FIG. 1.
Figure 13:
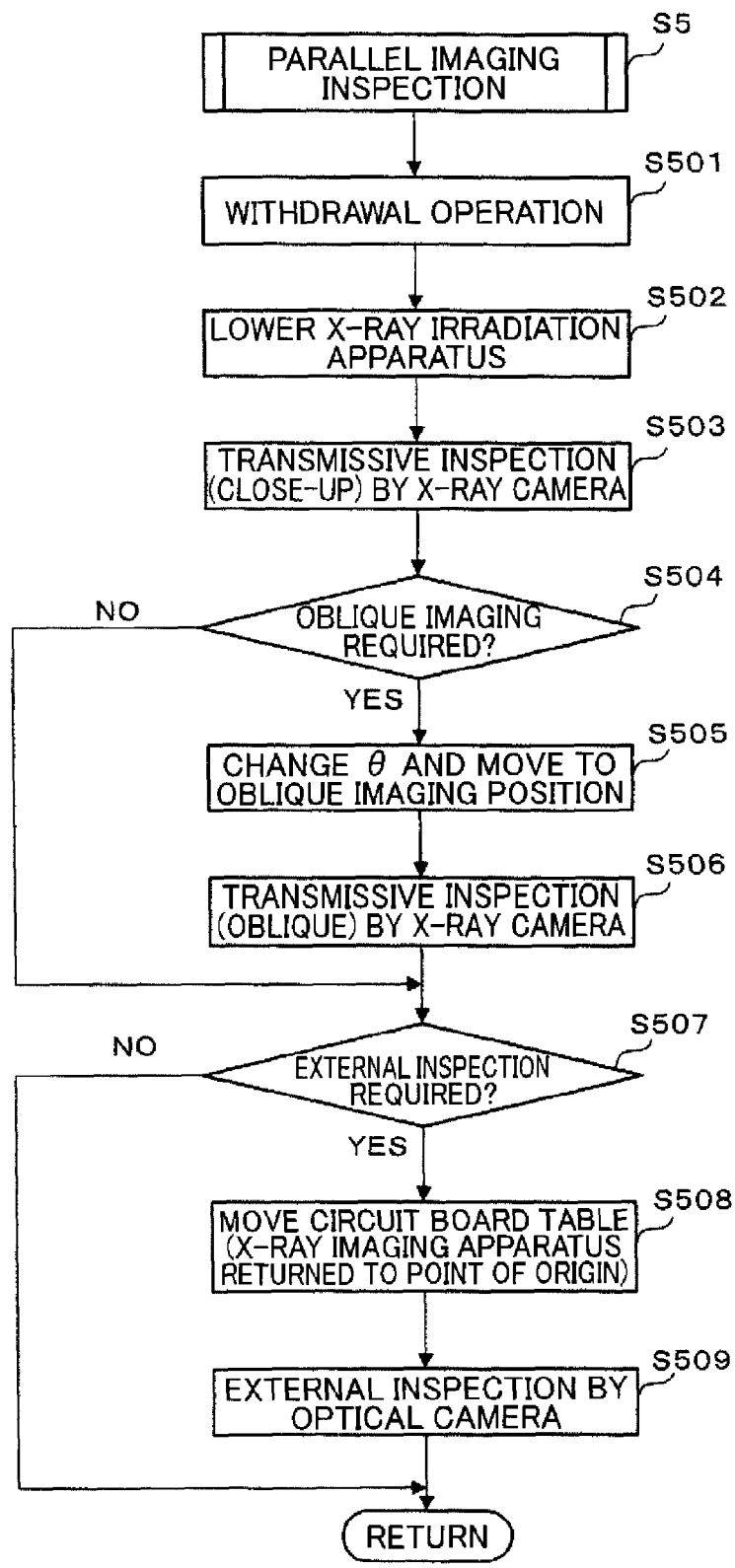
FIG. 13 is a flowchart showing a parallel imaging inspection sub-routine in FIG. 12.

Referring to FIG. 1, FIG. 12 and FIG. 14, firstly, the main control unit 601 executes a substrate reception operation (step S1). In this substrate reception operation, when a printed substrate W that has completed upstream steps is conveyed from the substrate conveyance conveyor 12, the shutter mechanism of substrate gateway 11*d* opens, and the printed substrate W is received. In this case, the substrate table 60 is adapted to be driven by the X axis motor 114*b* of the X axis ball screw mechanism 114, and to move to the side of substrate gateway 11*d*, so that the printed substrate W that has carried-in from the substrate conveyance conveyor 12 is received. Where the complex inspection device 10 is used in a high-variety small-volume production environment, the carried-in printed substrate W has various widths. However, in this carry-in and reception operation, the interval adjustment mechanism 90 of the substrate table 60 is operated to adjust the opposition interval between the two frame bodies 71, 72 of the conveyor unit 70 to a dimension suited to the width of the carried-in printed substrate W, on the basis of the communications data acquired previously from the host computer (not illustrated in FIG. 14). The printed substrate W which has carried-in via substrate gateway 11*d*, is carried-in onto the substrate table 60 by the conveyor drive mechanism 80 of the conveyor unit 70. After the carry-in operation, the shutter mechanism on the carry-in side is operated to close substrate gateway 11*d*, so as to prevent leaking of X-rays during X-ray imaging.

The printed substrate W is clamped and held between the two frame bodies 71, 72 of the conveyor unit 70, by the clamp unit 75 of the conveyor unit 70 (step S2), at a place where the carried-in printed substrate W has moved to a prescribed position.

When the printed substrate W is clamped, the substrate table 60 is driven again by the X axis motor 114*b* of the X axis ball screw mechanism 114, and is moved to a prescribed position inside the complex inspection device 10. Consequently, the printed substrate W is disposed at the inspection position. In parallel with this operation of the substrate table 60, the X axis motor 44*a* and the Y axis motor 48*a* of the camera unit 40 are respectively operated and the X-ray camera 50 is moved to a predetermined imaging position for the purpose of X-ray imaging. Since the R axis motor 170 of the X-ray radiation apparatus 160 may move or may not move at this timing, this arbitrary state is indicated by the broken line in FIG. 14.

Next, for inspection, the main control unit 601 judges as to whether or not it is required to withdraw the optical imaging apparatus 300 (step S4). The main control unit 601 is programmed with a constraint to judge that the withdrawal of the optical imaging apparatus 300 is required, in a case where it is necessary to capture close-up X-ray images based on X-rays from perpendicularly above the printed substrate W or to capture oblique X-ray images (oblique imaging) based on X-rays having a prescribed direction angle and a prescribed elevation angle. When withdrawal is required, the main control unit 601 executes a parallel imaging inspection sub-routine (step S5). When withdrawal is not required, on the contrary, the main control unit 601 executes a coaxial imaging inspection sub-routine (step S6). The parallel imaging inspection sub-routine is described below. The details of the coaxial imaging inspection sub-routine will be omitted here because the coaxial imaging inspection sub-routine is an inspection mode, which is substantially similar to the prior art technology, wherein the mirror 302*b* of the optical system 302 of the optical imaging apparatus 300 is arranged coaxially between the inspection object portion of the printed substrate W and the X-ray irradiation unit 160, and transmissive inspection based on X-ray images captured by the X-ray camera 50 and external inspection based on optical images captured by the CCD camera 301 are carried out simultaneously. Both of the parallel imaging inspection sub-routine and the coaxial imaging inspection sub-routine are carried out respectively for each area, a unit size of which is a field of view which is available to capture by the X-ray camera 50 and the CCD camera 301 in one imaging action.

After carrying out the parallel imaging inspection sub-routine (step S5) or the coaxial imaging inspection sub-routine (step S6), the main control unit 601 judges as to whether or not imaging has completed in all of the areas (step S7). If an un-captured area still remains, the main control unit 601 will transfer to step S3 and repeats the processing described above. In the present embodiment, since both non-close-up positional X-ray imaging with wide angle and close-up positional close-up X-ray imaging may be required for the same inspection object portion, the main control unit 601 transfers to step S3 and repeating the processing described above in the judgment in step S7 until all of the required imaging inspection is completed for that area, presuming that an un-captured area still remains, even if the area is the same.

Furthermore, if imaging for all of the areas has completed, the main control unit 601 executes processing for moving the printed substrate W that has been inspected, to a carry-out position (step S8). In this carry-out operation, the X axis drive unit 110 of the table-driving mechanism 100 is operated again and the substrate table 60 is driven along the X axis direction to the downstream side of the substrate conveyance direction (in the example depicted in the drawings, a direction towards substrate gateway 11*e*; see FIG. 2, etc.). When the substrate table 60 faces the substrate gateway 11*e* on the carry-out side, and the movement of the substrate table 60 is stopped, the clamp of the substrate table 60 is released (step S9) and a carry-out operation is carried out (step S10). In this carry-out operation, the shutter mechanism on the carry-out side is activated and the substrate gateway 11*e* is opened. Then, the conveyor drive mechanism 80 and the substrate conveyance conveyors 73, 74 are activated, so that the inspected printed substrate W is carried out to the substrate conveyance conveyor 14 on the carry-out side. After this carry-out operation, the shutter mechanism is operated to close substrate gateway 11*e*, and at the same time, in order to transfer to the next operation, the X axis drive unit 110 of the table-driving mechanism 100 is activated again, and the substrate table 60 is driven along the X axis direction to the upstream side of the substrate conveyance direction (in the example depicted in the drawings, a direction approaching substrate gateway 11*d*; see FIG. 2, etc.).

The main control unit 601 judges as to whether or not inspection of all of the printed substrates W has completed after the carry-out operation S10 (step S11). When an unprocessed printed substrate W remains, the main control unit 601 will move on to step S1 for repeating the processing described above. When inspection of all of the printed substrates W has completed, then the processing is terminated.

Next, the details of a parallel imaging inspection will be described with reference to FIG. 7, FIG. 8, FIG. 13 and FIG. 14.

In recent years, with development of high integration of printed substrates W, the electronic components mounted on the printed substrate W are also considerably smaller. This leads an increasing demand for close-up imaging of the inspection object portion where the X-ray irradiation unit 160 approaches near to the printed substrate W. In the present embodiment, in order to attain this close-up imaging, the optical imaging apparatus 300 is moved out by the optical drive mechanism 180 so that the X-ray irradiation unit 160 approaches near to the printed substrate W (step S501), in a case where the optical imaging apparatus 300 is in the imaging position.

More specifically, the main control unit 601 initially activates the X axis motor 185*b*, which forms the ball screw mechanism 185 of the optical drive mechanism 180, to move the slider 184, which carries the optical imaging apparatus 300, from the position shown in FIG. 9 to the position shown in FIG. 8. Consequently, the optical imaging apparatus 300 moves out from the imaging position shown in FIG. 9 to the withdrawn position shown in FIG. 8.

Then, the main control unit 601 activates the Z axis motor 155*b* which forms the ball screw mechanism 155 incorporated into the X-ray source supporting mechanism 150, so as to lower the slider 154 from the position shown in FIG. 9 to the position shown in FIG. 8 (step S502). Consequently, the X-ray irradiation unit 160 which is carried on the slider 154 is lowered from the non-close-up position in FIG. 9 to the close-up position shown in FIG. 8. In the example illustrated, in the close-up position, the X-ray irradiation unit 160 faces the downstream side of the optical imaging apparatus 300, in the X axis direction.

In this state, the main control unit 601 operates the X-ray camera 50 and captures a close-up X-ray image (step S503). Consequently, it is possible to obtain a large-magnification X-ray (transmissive) image, which is demanded in recent years.

Next, for capturing an X-ray image, the main control unit 601 determines as to whether or not necessary to capture a close-up X-ray image based on X-rays from perpendicularly above the printed substrate W, or to capture an oblique X-ray image (oblique imaging) based on X-rays having a prescribed direction angle and prescribed elevation angle (step S504). Where it is necessary to carryout oblique imaging, in order to obtain an oblique X-ray image based on X-rays having a prescribed direction angle and a prescribed elevation angle at the prescribed location on the printed substrate W, the main control unit 601 either leaves the R axis motor 170 in a halted state or operates the R axis motor 170 to alter the Z axis rotational position of the X-ray radiation apparatus 200. Simultaneously, the main control unit 601 respectively activates the X axis ball screw mechanism 44 of the X-ray camera unit 40 and the X axis motors 44*a*, 48*a* of the Y axis ball screw mechanism 48, so as to change the imaging position of the X-ray camera 50 as shown in, for example, FIG. 7. The main control unit 601 thus moves and positions the substrate table 60 in the X axis direction and the Y axis direction by the table-driving mechanism 100 (step S505).

In this state, the main control unit 601 activates the X-ray camera 50 to capture either a close-up X-ray image based on X-rays from perpendicularly above the printed substrate W or an oblique X-ray image, thereby executing transmissive inspection on the basis of the captured images (step S506). The inspection results are stored in the auxiliary storage device of the storage apparatus 602. If there are a plurality of prescribed locations (areas) on the printed substrate W or a plurality of prescribed direction angles and prescribed elevation angles, step S505 and step S506 are repeated for each combination of these parameters.

Here, in the present embodiment, it is sought to improve the efficiency of the inspection process by using a method such as the following.

Referring to FIG. 7 and FIG. 8, while the X-ray camera 50 is carrying out close-up imaging, the optical imaging apparatus 300 is moved out to the withdrawn position, as shown in FIG. 8. In a case where a plurality of prescribed inspection object locations for the X-ray camera 50 exists, namely, inspection object portions (areas) on the printed substrate W exist, and/or a plurality of prescribed direction angles or prescribed elevation angles exist(s), external inspection may still be possible by moving the substrate table 60 from a position below the imaging position to a position below the withdrawn position, yet leaving the optical imaging apparatus 300 at the withdrawn position, after capturing X-ray images in a perpendicular direction with respect to the printed substrate W or oblique images, for all of these combinations of directions and angles with respect to a close-up position or a non-close-up position.

In view of the foregoing, in the present embodiment, after the X-ray camera 50 has captured close-up imaging, or the like, external inspection will be carried out with the optical imaging apparatus 300 set back to the withdrawn position.

More specifically, the main control unit 601 judges as to whether or not external inspection is required (step S507). If the external inspection is required, the table-driving mechanism 100 is activated, so that the substrate table 60 is moved, and the inspection object portion of the printed substrate W held on the substrate table 60 is moved to directly below the optical system 302 of the optical imaging apparatus 300 which has moved out to the withdrawn position (step S508). In the present embodiment, the X-ray irradiation unit 160 is configured to be moved to the non-close-up position, at this time.

When the movement of the substrate table 60 is completed, the optical imaging apparatus 300 is operated, so that an optical image is captured, and external inspection of the inspection object portion is carried out on the basis of this optical image (step S509). More specifically, the inspection object portion is illuminated by LEDs in the hood 302a of the optical system, and light reflected from the inspection object portion is reflected by the mirror 302b and directed to the CCD camera 301, whereby an optical image of the inspection object portion is captured by the CCD camera 301 on the basis of this reflected light. If a plurality of inspection object portions (areas) on the printed substrate W exists, step S508 and step S509 are repeated in accordance with the number of the object portions (areas).

When the optical imaging operation has completed, or when the external inspection is not necessary in step S507, then the control of the main control unit 601 reverts to the main routine. With respect to the laser inspection apparatus 400, the apparatus 400 enables carrying out height inspection at a fixed position regardless of the movement of the X-ray imaging apparatus and the optical imaging apparatus 300. Therefore, by moving the substrate table 60, the required inspection can be carried out suitably, as well as the external inspection in the parallel imaging inspection sub-routine (step S5).

As described above, according to the present embodiment, where inspecting a printed substrate W on which a plurality of electronic components is mounted, and the X-ray irradiation unit is in the non-close-up position, the optical drive mechanism 180 serving as drive means enables setting the optical imaging apparatus 300 to the imaging position. Therefore, similarly to the prior art technology, the present embodiment enables simultaneously carrying out both external inspection based on images of visible light captured by the optical imaging apparatus 300 and transmissive inspection based on X-ray images captured by the X-ray camera 50 on the same printed substrate W in a parallel fashion. Moreover, in the present embodiment, the optical imaging apparatus 300 is configured to be placed to the withdrawn position by the optical drive mechanism 180 which serves as drive means. Therefore, the Z axis ball screw mechanism 155, which serves as magnification changing means (lifting apparatus), enables to switch the magnification of the X-ray image. Accordingly, it is possible to respond to the various imaging requirements which have been demanded in recent years. That is, the optical imaging apparatus 300 according to the present embodiment is configured to be movable between an imaging position, and a withdrawn position which is moved out from the imaging position, by the optical drive mechanism 180 which serves as drive means. Where it is necessary to move at least one of the X-ray irradiation unit 160 and the X-ray camera 50 (in the present embodiment, the X-ray irradiation unit 160) to the close-up position, the optical drive mechanism 180 is controlled by the control unit 600 which serves as imaging position control means such that the optical imaging apparatus 300 is moved out to the withdrawn position. Therefore the X-ray irradiation unit 160 is able to move to the close-up position near to the printed substrate W, without being obstructed by the optical imaging apparatus 300. Consequently, it is possible to obtain high-magnification close-up X-ray images which have been required in recent years. Furthermore, both the capture of X-ray transmissive images with the X-ray irradiation unit 160 located in the non-close-up position, and the capture of images by the optical imaging apparatus 300 can be carried out simultaneously in parallel fashion, while the printed substrate W is held at the same position. Moreover, where the X-ray irradiation unit 160 is set to the close-up position, the X-ray irradiation unit 160 does not collide with the optical imaging apparatus 300. Furthermore, during the capture of X-ray transmissive images with the X-ray irradiation unit 160 at the close-up position, the capture of images is carried out for an inspection object portion located at the same position. Therefore, inspection can be performed on the basis of images of three types, namely, a non-close-up X-ray image, a close-up X-ray image and an optical image, captured with high accuracy at the inspection object portion.

In the present embodiment, for capturing images of the inspection object portion by the optical imaging apparatus 300 at the withdrawn position, there is provided a table-driving mechanism 100 which moves the substrate table 60 in a plane parallel to the substrate table 60, and a control unit 600 which serves as table movement control means for controlling the table-driving mechanism 100 such that the inspection object portion is positioned below the optical imaging apparatus 300 located in the withdrawn position, or below the mirror 302b. Therefore, in the present embodiment, when the optical imaging apparatus 300 is moved out to the withdrawn position, the printed substrate W can be conveyed to a position where an image of the inspection object portion can be captured by the optical imaging apparatus 300 located at the withdrawn position. Therefore, the X-ray camera 50 enables capturing a transmissive image in the close-up position in a state where the printed substrate W is positioned in a middle region between the X-ray radiation apparatus 200 and the X-ray camera 50. After capturing this transmissive image, the optical imaging apparatus 300 enables carrying out external inspection of the printed substrate W by positioning the printed substrate W below the optical imaging apparatus 300 which is located in the withdrawn position that is outside the aforementioned region. Consequently, the optical imaging apparatus 300 itself does not need to be moved, and the operating rate of the optical imaging apparatus 300 will be raised, thereby contributing to shortening of the inspection time.

In the present embodiment, there is provided a table-driving mechanism 100 configured to move the substrate table 60, which holds the printed substrate W, in a plane parallel to the substrate table 60 along both directions: the prescribed direction (X axis direction) and a direction (Y axis direction) perpendicular to the prescribed direction. The table-driving mechanism 100 moves the plurality of inspection object portions on the printed substrate W within a region between the X-ray radiation apparatus 200 of the X-ray irradiation unit 160 and the X-ray camera 50, for each predetermined area. In either case where the X-ray irradiation unit 160 exists at the non-close-up position or the close-up position, the X-ray camera 50 captures respective X-ray images of the inspection object portion. On the other hand, the optical imaging apparatus 300 captures optical images of the inspection object portion at the imaging position, when the X-ray irradiation unit 160 is at the non-close-up position. Consequently, even if a plurality of inspection object portions exist, it is yet possible to obtain a non-close-up X-ray image, a close-up X-ray image, and an optical image, for each of the inspection object portions. The "predetermined area" mentioned above is set as necessary in accordance with the imaging conditions. For example, where X-ray images at a certain magnification are captured, the printed substrate W may be divided into an area in accordance with a field of view of the X-ray camera 50 at that magnification. In this example, each divisional range is set as one area, so that the substrate table 60 may be moved for sequentially capturing images of all of the areas. The same applies to a case where the optical imaging apparatus 300 captures images. There is a case where the inspection object portion is individual solder balls of electronic components, or the like, where a plurality of inspection object portions would be encompassed within one area. Meanwhile, in external inspection, and the like, there is a case where the inspection object portion would be a partial region of the printed substrate W. In the aforementioned cases, the substrate table 60 may be moved for each region, or for each inspection object portion.

Where non-close-up X-ray images, close-up X-ray images and optical images are captured for a plurality of inspection object portions, capture of the non-close-up X-ray images and capture of the optical images may initially be carried out in parallel (called "parallel imaging" below) for each of the plurality of inspection object portions, and close-up X-ray images may be captured for each of the inspection object portions. Where parallel imaging is carried out, the X-ray irradiation unit 160 is situated at the non-close-up position and the optical imaging apparatus 300 is situated at the imaging position. Parallel imaging is then carried out for each of the plurality of inspection object portions, by moving, as necessary, the substrate table 60 to each of the predetermined areas. Where a close-up X-ray image is captured after the parallel imaging, the optical imaging apparatus 300 is moved to the withdrawn position and the X-ray irradiation unit 160 is situated in the close-up position. Capture of close-up X-ray images is then carried out for each of the plurality of inspection object portions, by moving, as necessary, the substrate table 60 to each of the predetermined areas. Consequently, the efficiency of the imaging operation is improved.

Figure 16:
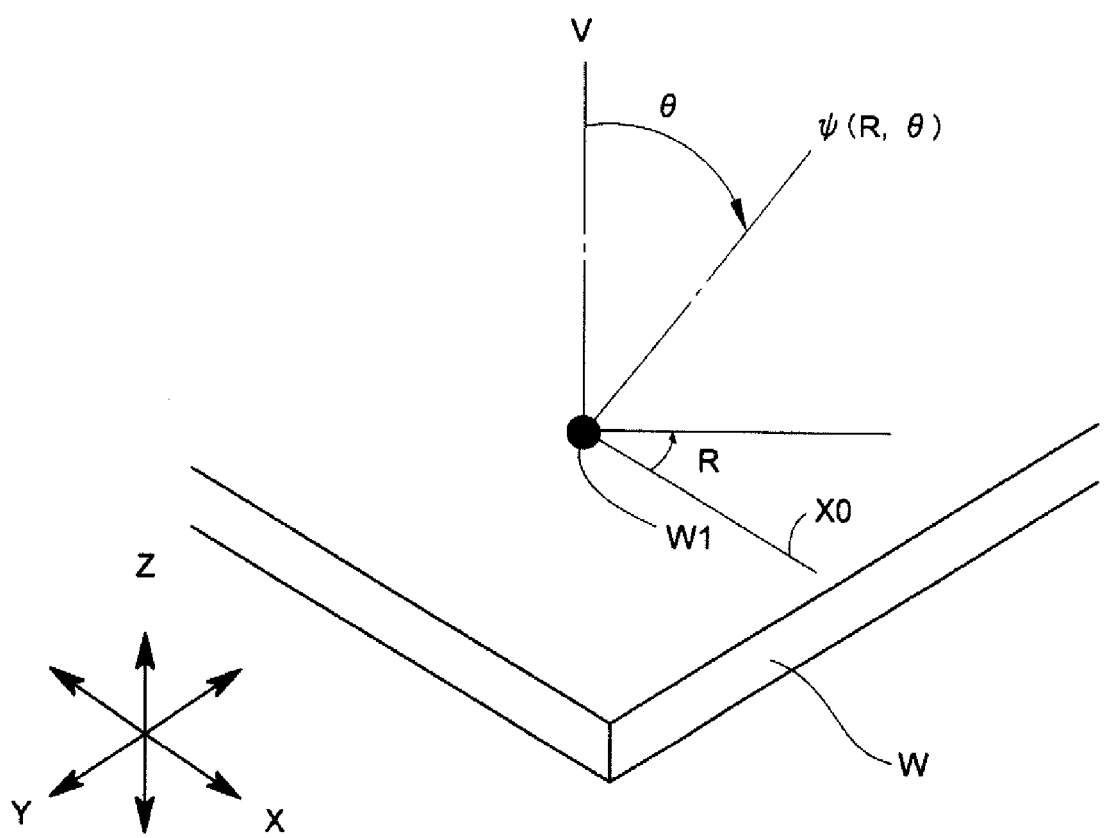
FIG. 16 is an illustrative diagram of the traveling direction.

In the present embodiment, X-ray camera movement means 49 is provided to move the X-ray camera 50 in both the X axis direction and the Y axis direction, in a plane parallel to the printed substrate W. Therefore, the capture of so-called oblique images by the X-ray camera movement means 49 is also facilitated. To give an example of the capture of oblique images, a traveling direction $\psi$ (R, $\theta$) of the X-rays, as shown in FIG. 16, is set on the basis of a direction angle R selected about the vertical axis V of which an origin is defined at the inspection object portion W1, and an angle of inclination (elevation angle) $\theta$ formed with the vertical axis V, thereby performing X-ray imaging along the set traveling direction $\psi$ (R, $\theta$). The direction angle R is defined as an angle obtained, for example, by rotation from 0° defined on a reference axis Xo passing through an inspection object portion W1 as an origin. Where oblique images are captured along the traveling direction $\psi$ (R, $\theta$), such an operation may be attained, in the present embodiment, by the imaging position control means (control unit 600) so that: the drive means (optical drive mechanism 180) is controlled to set back the optical imaging apparatus 300 to the withdrawn position in advance; the X-ray camera 50 is positioned on a line of extension of the X-rays along the traveling direction $\psi$ (R, $\theta$) from the X-ray source by the X-ray camera movement means 49; and the substrate table 60 is positioned by the table-driving mechanism 100 so that the X-rays travel along the traveling direction $\psi$ (R, $\theta$) passing through the inspection object portion W1.

In this state, the X-ray irradiation unit 160 is situated in the non-close-up position, and a non-close-up X-ray image is captured. The X-ray irradiation unit 160 is situated in the close-up position and a close-up X-ray image is captured. These operations are carried out for each of the plurality of inspection object portions. Consequently, without being obstructed by the optical imaging apparatus 300, an oblique image with respect to a prescribed direction about the up/down axis can be captured for each inspection object portion, by a traveling direction $\psi$ (R, $\theta$) which is previously set in respect of each of a plurality of inspection object portions W1.

Furthermore, in the present embodiment, the X-ray irradiation unit 160 is provided with an R axis motor 170 which rotates the X-ray radiation apparatus 200 that irradiates X-rays about the Z axis (up/down axis). The R axis motor 170 is rotation-controlled such that the X-ray camera 50 can capture an oblique image in a prescribed traveling direction $\psi$ (R, $\theta$) with respect to a prescribed inspection object portion, and such that X-rays irradiated from the X-ray radiation apparatus 200 pass through the inspection object portion along the prescribed traveling direction $\psi$ (R, $\theta$) and the X-rays arrive at the X-ray camera 50.

Consequently, even if an irradiation direction of the X-rays of the X-ray radiation apparatus 200 is directional, the directional characteristics may be fit to the traveling direction $\psi$ (R, $\theta$) by rotating the X-ray radiation apparatus 200 about the Z axis. Accordingly, there is great freedom in the setting of the traveling direction, so that oblique imaging can be carried out by setting, with broader setting range, the traveling direction for each one of the plurality of inspection object portions.

The present disclosure is not limited to the embodiment described above, and needless to say, various modifications can be applied within a scope that does not depart from the essence of the present disclosure.

For example, in the present embodiment, the X-ray camera 50 is disposed below the substrate table 60 and the X-ray irradiation unit 160 is disposed above the substrate table 60, but it is also possible to dispose the X-ray camera 50 above the substrate table 60 and to dispose the X-ray irradiation unit 160 below the substrate table 60.

Furthermore, in the present embodiment, an arrangement is adopted in which the X-ray irradiation unit 160 is moved up and down by the X-ray source supporting mechanism 150, but it is also possible to adopt an arrangement in which the X-ray irradiation unit 160 is fixed at a constant position, and the X-ray camera 50 can be driven in the Z axis direction.

Moreover, in the present embodiment, in order to face the inspection object portion towards the optical imaging apparatus 300 which is in the withdrawn position, the substrate table 60 is configured to be movable in the X and Y axis directions, but it is also possible to form the optical imaging apparatus 300 so as to be movable within the area of the withdrawn position.

As described above, the present disclosure is a complex inspection device for a printed substrate, comprising: a substrate table configured to place a printed substrate on which a plurality of electronic components is mounted; an optical imaging apparatus configured to capture an optical image of an inspection object portion of the printed substrate placed on the substrate table; an X-ray irradiation unit configured to irradiate X-rays onto the inspection object portion; an X-ray camera configured to capture an X-ray image of the inspection object portion from X-rays traveling through the printed substrate; magnification changing means for changing a magnification of the X-ray image by relatively displacing the X-ray irradiation unit and the X-ray camera within a range between a close-up position where an arrival path of X-rays arriving at the X-ray camera from the X-ray irradiation unit has a first distance for close-up imaging, and a non-close-up position where the arrival path has a distance longer than the first distance; drive means for moving the optical imaging apparatus between an imaging position where the optical imaging apparatus faces the inspection object portion at a space between the X-ray irradiation unit and the X-ray camera, and a withdrawn position to which the optical imaging apparatus is moved out from the imaging position so that the X-ray irradiation unit and the X-ray camera enables to relatively move toward the close-up position; and imaging position control means for controlling the drive means such that, where at least one of the X-ray irradiation unit or the X-ray camera is required to move, the optical imaging apparatus is moved out in advance to the withdrawn position.

A desirable mode of a complex inspection device for a printed substrate further comprises: a table-driving mechanism configured to move the substrate table in a plane parallel to the substrate table, such that the optical imaging apparatus placed to the withdrawn position is allowed to capture an image of the inspection object portion; and table movement control means which controls the table-driving mechanism so as to capture an image of the inspection object portion at the withdrawn position, where the optical imaging apparatus has moved out to the withdrawn position. In this mode, the optical imaging apparatus can be operated and external inspection of the printed substrate can be carried out, when the optical imaging apparatus has moved to a withdrawn position in order for the X-ray camera to capture a transmissive image at the close-up position. Therefore, it is possible to raise the operating rate of the optical imaging apparatus, thus contributing to shortening of the inspection time.

A further mode of the present disclosure comprises: an optical imaging apparatus disposed above a printed substrate on which a plurality of electronic components is mounted, the optical imaging apparatus including an optical system having a light receiving unit permitting transmission of X-rays, the optical imaging apparatus being configured to capture an optical image of an inspection object portion obtained from the optical system; an X-ray irradiation unit configured to irradiate X-rays onto the inspection object portion from above; an X-ray camera configured to capture an X-ray image of the inspection object portion by receiving X-rays, traveling through the printed substrate, below the printed substrate; a lifting apparatus configured to adjust a height of the X-ray irradiation unit with respect to the printed substrate, within a range between a non-close-up position defined as a position above the optical imaging apparatus and a close-up position set below the optical system of the optical imaging apparatus; drive means for moving the optical imaging apparatus between an imaging position where the optical imaging apparatus being placed at a position at which the light receiving unit enables transmitting X-rays from the X-ray camera, the position being defined within a region from the X-ray irradiation unit located at the non-close-up position to the X-ray camera, and a withdrawn position where the optical imaging apparatus is moved out outside the region; and imaging position control means for controlling the drive means such that the optical imaging apparatus is moved out in advance to the withdrawn position, in a case where the X-ray irradiation unit is driven to move between the close-up position and the non-close-up position by the lifting apparatus, wherein the X-ray camera is configured to capture X-ray images of the inspection object portion on the printed substrate which is disposed inside the region, in both cases where the X-ray irradiation unit is in the non-close-up position and where the X-ray irradiation unit is in the close-up position, and wherein the optical imaging apparatus is configured to capture optical images of the inspection object portion in the imaging position in a case where the X-ray irradiation unit is in the non-close-up position.

In a desirable mode of a complex inspection device for a printed substrate, the printed substrate has a plurality of inspection object portions; and the complex inspection device further comprises: a substrate table which holds the printed substrate; and a table-driving mechanism configured to move the substrate table in both a prescribed direction and a direction perpendicular to the prescribed direction in a plane parallel to the substrate table; the table-driving mechanism is configured to position the plurality of inspection object portions within the region for each predetermined area; and the X-ray camera respectively captures X-ray images of the inspection object portion inside the region, when the X-ray irradiation unit is in both the non-close-up position and the close-up position, and the optical imaging apparatus captures optical images of the inspection object portion in the region, at the imaging position, when the X-ray irradiation unit is in the non-close-up position. According to this mode, even if there is a plurality of inspection object portions, it is possible to obtain a non-close-up X-ray image, a close-up X-ray image and an optical image, respectively for each of the inspection object portions.

A desirable mode of a complex inspection device for a printed substrate further comprises X-ray camera movement means which moves the X-ray camera in both of the directions in a plane parallel to the printed substrate; wherein, where capturing an oblique image is required, the oblique image being referred to as an image is captured by an X-ray traveling through the inspection object portion along a traveling direction, the traveling direction being determined for each inspection object portion, determination of the traveling direction being on the basis of a predetermined direction angle about a vertical axis wherein the respective inspection object portions are defined as an origin of the vertical axis, and on the basis of an angle of inclination with respect to the vertical axis at each inspection object portion; the imaging position control means is configured to control the drive means such that the optical imaging apparatus is moved out in advance to the withdrawn position; the table mechanism is configured to position the substrate table such that X-rays are traveling through the inspection object portion along the traveling direction; and the X-ray camera movement means is configured to position the X-ray camera such that X-rays are traveling through the inspection object portion along the traveling direction, in a state where the X-ray irradiation unit is positioned in either one of the non-close-up position and the close-up position. According to this mode, it is possible to capture oblique X-ray images in a broad range about a vertical axis by the X-ray camera, in one or more inspection object portions on the printed substrate. Furthermore, it is also possible to position the X-ray irradiation unit at the non-close-up position and to capture an oblique image with high magnification and a relatively small elevation angle (angle of inclination), and to position the X-ray irradiation unit at the close-up position and to capture an oblique image with even higher magnification and a large elevation angle (angle of inclination).

In a desirable mode of a complex inspection device for a printed substrate, the X-ray irradiation unit comprises an R axis motor configured to rotate an X-ray radiation apparatus irradiating X-rays about a vertical axis, and the motor control device is provided with a control device to control rotation of the R axis motor such that directional characteristics of the X-ray radiation apparatus fits the traveling direction of the oblique image, when capturing the oblique image. In this mode, even with an X-ray radiation apparatus having directional characteristics in the irradiation of X-rays, it is possible to match the directional characteristics with the traveling direction, by rotating the X-ray radiation apparatus about the vertical axis. Accordingly, there is great freedom in the setting of the traveling direction, and oblique imaging can be carried out by setting the traveling direction in an even broader setting range, for each one of the plurality of inspection object portions. The present disclosure is not limited to the embodiment described above, and needless to say, various modifications can be applied within a scope that does not depart from the essence of the present disclosure.

INDUSTRIAL APPLICABILITY

The present disclosure is suitable for X-ray inspection of a printed substrate that has been produced, in equipment for manufacturing printed substrates, or the like.

The invention claimed is:

1. A complex inspection device for a printed substrate, comprising:
   a substrate table configured to support a printed substrate on which a plurality of electronic components are mounted;
   an optical imaging apparatus configured to capture an optical image of an inspection object portion of the printed substrate placed on the substrate table;
   an X-ray irradiation unit configured to irradiate X-rays onto the inspection object portion;
   an X-ray camera configured to capture an X-ray image of the inspection object portion from X-rays traveling through the printed substrate;
   a magnification changing unit configured to change a magnification of the X-ray image by relatively displacing the X-ray irradiation unit and the X-ray camera within a range between a close-up position where an arrival path of X-rays arriving at the X-ray camera from the X-ray irradiation unit has a first distance for close-up imaging, and a non-close-up position where the arrival path has a distance longer than the first distance;
   a drive unit configured to move the optical imaging apparatus between an imaging position where the optical imaging apparatus faces the inspection object portion at a space between the X-ray irradiation unit and the X-ray camera, and a withdrawn position to which the optical imaging apparatus is moved out from the imaging position so that the X-ray irradiation unit and the X-ray camera are enabled to relatively move toward the close-up position;
   an imaging position control unit configured to control the drive unit such that, where at least one of the X-ray irradiation unit or the X-ray camera is required to move, the optical imaging apparatus is moved out in advance to the withdrawn position;
   a table-driving mechanism configured to move the substrate table in a plane parallel to the substrate table, such that the optical imaging apparatus placed in the withdrawn position is allowed to capture an image of the inspection object portion; and
   a table movement control configured to control the table-driving mechanism so as to capture an image of the inspection object portion at the withdrawn position, where the optical imaging apparatus has moved out to the withdrawn position.

2. The complex inspection device for a printed substrate according to claim 1, wherein, where the optical imaging apparatus has moved out to the withdrawn position, the X-ray irradiation unit and the X-ray camera are configured to be relatively positioned to the close-up position, the substrate table is configured to be positioned between the X-ray irradiation unit and the X-ray camera, and thereby carrying out X-ray imaging of the inspection object portion.

3. The complex inspection device for a printed substrate according to claim 1, configured to carry out X-ray imaging of the inspection object portion by relatively setting the X-ray irradiation unit and the X-ray camera to the non-close-up position and positioning the substrate table between the X-ray irradiation unit and the X-ray camera, and configured to carry out optical imaging of the inspection object portion by moving the optical imaging apparatus in the imaging position.

4. The complex inspection device for a printed substrate according to claim 1, further comprising an X-ray camera movement unit for moving the X-ray camera in both of the directions in a plane parallel to the printed substrate, wherein
   where capturing an oblique image is required, the oblique image being referred to as an image is captured by an X-ray traveling through the inspection object portion along a traveling direction, the traveling direction being determined for each inspection object portion, determination of the traveling direction being on a basis of a predetermined direction angle about a vertical axis wherein the respective inspection object portions are defined as an origin of the vertical axis, and on a basis of an angle of inclination with respect to the vertical axis at each inspection object portion,
   the imaging position control unit is configured to control the drive unit such that the optical imaging apparatus is moved out in advance to the withdrawn position,
   the table-driving mechanism is configured to position the substrate table such that X-rays are traveling through the inspection object portion along the traveling direction; and
   the X-ray camera movement unit is configured to position the X-ray camera such that X-rays are traveling through the inspection object portion along the traveling direction, in a state where the X-ray irradiation unit is positioned in either one of the non-close-up position and the close-up position.

5. The complex inspection device for a printed substrate according to claim 4, wherein the X-ray irradiation unit comprises an R axis motor configured to rotate an X-ray radiation apparatus irradiating X-rays about a vertical axis,
   the complex inspection device further comprising a control unit for controlling rotation of the R axis motor such that directional characteristics of the X-ray radiation apparatus fits the traveling direction of the oblique image, when capturing the oblique image.

6. The complex inspection device for a printed substrate according to claim 2, configured to carry out X-ray imaging of the inspection object portion by relatively setting the X-ray irradiation unit and the X-ray camera to the non-close-up position and positioning the substrate table between the X-ray irradiation unit and the X-ray camera, and configured to carry out optical imaging of the inspection object portion by moving the optical imaging apparatus in the imaging position.

7. The complex inspection device for a printed substrate according to claim 2, further comprising an X-ray camera movement unit for moving the X-ray camera in both of the directions in a plane parallel to the printed substrate, wherein
   where capturing an oblique image is required, the oblique image being referred to as an image is captured by an X-ray traveling through the inspection object portion along a traveling direction, the traveling direction being determined for each inspection object portion, determination of the traveling direction being on a basis of a predetermined direction angle about a vertical axis wherein the respective inspection object portions are defined as an origin of the vertical axis, and on a basis of an angle of inclination with respect to the vertical axis at each inspection object portion, the imaging position control unit is configured to control the drive unit such that the optical imaging apparatus is moved out in advance to the withdrawn position, the table-driving mechanism is configured to position the substrate table such that X-rays are traveling through the inspection object portion along the traveling direction; and the X-ray camera movement unit is configured to position the X-ray camera such that X-rays are traveling through the inspection object portion along the traveling direction, in a state where the X-ray irradiation unit is positioned in either one of the non-close-up position and the close-up position.

8. The complex inspection device for a printed substrate according to claim 3, further comprising an X-ray camera movement unit for moving the X-ray camera in both of the directions in a plane parallel to the printed substrate, wherein where capturing an oblique image is required, the oblique image being referred to as an image is captured by an X-ray traveling through the inspection object portion along a traveling direction, the traveling direction being determined for each inspection object portion, determination of the traveling direction being on basis of a predetermined direction angle about a vertical axis wherein the respective inspection object portions are defined as an origin of the vertical axis, and on a basis of an angle of inclination with respect to the vertical axis at each inspection object portion, the imaging position control unit is configured to control the drive unit such that the optical imaging apparatus is moved out in advance to the withdrawn position, the table-driving mechanism is configured to position the substrate table such that X-rays are traveling through the inspection object portion along the traveling direction; and the X-ray camera movement unit is configured to position the X-ray camera such that X-rays are traveling through the inspection object portion along the traveling direction, in a state where the X-ray irradiation unit is positioned in either one of the non-close-up position and the close-up position.

* * * * *